United States Patent
Dams et al.

(10) Patent No.: US 9,701,889 B2
(45) Date of Patent: *Jul. 11, 2017

(54) METHODS FOR TREATING SILICICLASTIC HYDROCARBON-BEARING FORMATIONS WITH FLUORINATED AMINE OXIDES

(75) Inventors: Rudolf J. Dams, Antwerp (BE); Yong K. Wu, Woodbury, MN (US); Steven J. Martin, Shoreview, MN (US); Douglas E. Johnson, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 595 days.

This patent is subject to a terminal disclaimer.

(21) Appl. No.: 13/979,747

(22) PCT Filed: Jan. 13, 2012

(86) PCT No.: PCT/US2012/021165
§ 371 (c)(1),
(2), (4) Date: Oct. 1, 2013

(87) PCT Pub. No.: WO2012/125219
PCT Pub. Date: Sep. 20, 2012

(65) Prior Publication Data
US 2014/0014330 A1      Jan. 16, 2014

Related U.S. Application Data

(60) Provisional application No. 61/432,388, filed on Jan. 13, 2011.

(51) Int. Cl.
E21B 43/16        (2006.01)
C09K 8/584        (2006.01)
(Continued)

(52) U.S. Cl.
CPC ............ *C09K 8/584* (2013.01); *C07C 291/04* (2013.01); *C07C 311/05* (2013.01); *C09K 8/565* (2013.01);
(Continued)

(58) Field of Classification Search
CPC .......... E21B 47/06; E21B 43/26; E21B 47/00; E21B 44/005; E21B 43/16
(Continued)

(56) References Cited

U.S. PATENT DOCUMENTS 2,803,615 A    8/1957   Ahlbrecht
3,311,167 A    3/1967   O'Brien
(Continued)

FOREIGN PATENT DOCUMENTS

CA    2009732    8/1990
GB    2031482    4/1980
(Continued)

OTHER PUBLICATIONS

Adibhatla, "Effect of Surfactants on Wettability of Near-wellbore Regions of Gas Reservoirs", Journal of Petroleum Science and Engineering, 2006, vol. 52, pp. 227-236. (XP002519991).
(Continued)

*Primary Examiner* — Silvana Runyan

(57) ABSTRACT

A method of treating a siliciclastic, hydrocarbon-bearing formation includes contacting the hydrocarbon-bearing formation with a composition comprising solvent and a fluorinated amine oxide. The method can provide siliciclastic, hydrocarbon-bearing formations treated according to the method.

20 Claims, 3 Drawing Sheets

(51) Int. Cl.
C09K 8/565 (2006.01)
C09K 8/575 (2006.01)
C09K 8/80 (2006.01)
C07C 291/04 (2006.01)
C07C 311/05 (2006.01)

(52) U.S. Cl.
CPC ............ *C09K 8/575* (2013.01); *C09K 8/5751* (2013.01); *C09K 8/80* (2013.01); *E21B 43/16* (2013.01)

(58) Field of Classification Search
USPC .................. 166/250.01, 350.1, 307, 308
See application file for complete search history.

(56) References Cited

U.S. PATENT DOCUMENTS

| | | |
|---|---|---|
| 3,394,758 A | 7/1968 | Terry |
| 3,555,100 A | 1/1971 | Garth |
| 3,653,442 A | 4/1972 | Ross |
| 3,787,351 A | 1/1974 | Olson |
| 3,902,557 A | 9/1975 | Shaughnessy |
| 4,018,689 A | 4/1977 | Thompson |
| 4,147,851 A | 4/1979 | Raynolds |
| 4,200,154 A | 4/1980 | Tate |
| 4,329,236 A | 5/1982 | Alford |
| 4,432,882 A | 2/1984 | Raynolds |
| 4,440,653 A | 4/1984 | Briscoe |
| 4,460,791 A | 7/1984 | Cooke |
| 4,557,837 A | 12/1985 | Clark, III |
| 4,565,639 A | 1/1986 | Penny |
| 4,594,200 A | 6/1986 | Penny |
| 4,609,477 A | 9/1986 | Crema |
| 4,702,849 A | 10/1987 | Penny |
| 4,753,740 A | 6/1988 | Marlett |
| 4,767,545 A | 8/1988 | Karydas |
| 4,817,715 A | 4/1989 | Peru |
| 4,823,873 A | 4/1989 | Karydas |
| 4,921,619 A | 5/1990 | Karydas |
| 4,923,009 A | 5/1990 | Watkins |
| 4,993,448 A | 2/1991 | Karydas |
| 4,997,580 A | 3/1991 | Karydas |
| 5,042,580 A | 8/1991 | Cullick |
| 5,092,405 A | 3/1992 | Prukop |
| 5,129,457 A | 7/1992 | Sydansk |
| 5,186,257 A | 2/1993 | Stahl |
| 5,247,993 A | 9/1993 | Sarem |
| 5,310,002 A | 5/1994 | Blauch |
| 5,358,052 A | 10/1994 | Gidley |
| 5,468,353 A | 11/1995 | Anich |
| 5,852,148 A | 12/1998 | Behr |
| 6,165,948 A | 12/2000 | Dewenter |
| 6,182,759 B1 | 2/2001 | Burger |
| 6,206,102 B1 | 3/2001 | Pusch |
| 6,225,263 B1 | 5/2001 | Collins |
| 6,380,149 B2 | 4/2002 | Flynn |
| 6,579,572 B2 | 6/2003 | Espin |
| 6,649,571 B1 | 11/2003 | Morgan |
| 6,660,693 B2 | 12/2003 | Miller |
| 6,664,354 B2 | 12/2003 | Savu |
| 6,689,854 B2 | 2/2004 | Fan |
| 6,729,409 B1 | 5/2004 | Gupta |
| 6,911,417 B2 | 6/2005 | Chan |
| 6,945,327 B2 | 9/2005 | Ely |
| 6,972,274 B1 | 12/2005 | Slikta |
| 7,084,094 B2 | 8/2006 | Gunn |
| 7,141,537 B2 | 11/2006 | Audenaert |
| 7,165,613 B2 | 1/2007 | Chan |
| 7,417,099 B2 | 8/2008 | Savu |
| 7,547,732 B2 | 6/2009 | Moore |
| 7,585,817 B2 | 9/2009 | Pope |
| 7,629,298 B2 | 12/2009 | Arco |
| 7,772,162 B2 | 8/2010 | Pope |
| 7,855,169 B2 | 12/2010 | Pope |
| 8,043,998 B2 | 10/2011 | Pope |
| 8,138,127 B2 | 3/2012 | Pope |
| 8,176,981 B2 | 5/2012 | Savu |
| 8,236,737 B2 | 8/2012 | Fan |
| 8,261,825 B2 | 9/2012 | Pope |
| 8,418,759 B2 | 4/2013 | Moore |
| 8,476,385 B2 | 7/2013 | Dams |
| 8,629,089 B2 | 1/2014 | Dams |
| 8,678,090 B2 | 3/2014 | Baran, Jr. |
| 2003/0092581 A1 | 5/2003 | Crews |
| 2005/0244641 A1 | 11/2005 | Vincent |
| 2006/0045979 A1 | 3/2006 | Dams |
| 2006/0264334 A1 | 11/2006 | Gupta |
| 2007/0015669 A1 | 1/2007 | Zhang |
| 2007/0015864 A1 | 1/2007 | Hintzer |
| 2007/0029085 A1 | 2/2007 | Panga |
| 2007/0243389 A1 | 10/2007 | Audenaert |
| 2009/0281002 A1 | 11/2009 | Casper |
| 2010/0152071 A1 | 6/2010 | Pope |
| 2010/0181068 A1 | 7/2010 | Pope |
| 2010/0224361 A1* | 9/2010 | Pope ...................... C09K 8/584 166/250.02 |
| 2010/0270019 A1 | 10/2010 | Pope |
| 2010/0270020 A1 | 10/2010 | Baran, Jr. |
| 2010/0276142 A1 | 11/2010 | Skildum |
| 2010/0288498 A1* | 11/2010 | Moore et al. .............. 166/305.1 |
| 2011/0056689 A1 | 3/2011 | Baran, Jr. |
| 2011/0124532 A1 | 5/2011 | Maurer |
| 2011/0136704 A1 | 6/2011 | Sharma |
| 2011/0177983 A1 | 7/2011 | Baran, Jr. |
| 2011/0201531 A1 | 8/2011 | Sharma |
| 2011/0247823 A1 | 10/2011 | Dams |
| 2012/0071372 A1 | 3/2012 | Iaconelli |
| 2012/0097393 A1 | 4/2012 | Dams |
| 2013/0264061 A1 | 10/2013 | Baran, Jr. |
| 2013/0269932 A1 | 10/2013 | Dams |

FOREIGN PATENT DOCUMENTS

| | | |
|---|---|---|
| WO | WO 97/46283 | 12/1997 |
| WO | WO 00-47692 | 8/2000 |
| WO | WO 03-089540 | 10/2003 |
| WO | WO 2005-028589 | 3/2005 |
| WO | WO 2005-035936 | 4/2005 |
| WO | WO 2007-017806 | 2/2007 |
| WO | WO 2007-033489 | 3/2007 |
| WO | WO 2007-097975 | 8/2007 |
| WO | WO 2009085936 A1 * | 7/2009 |
| WO | WO 2010-132333 | 11/2010 |
| WO | WO 2010-132362 | 11/2010 |
| WO | WO 2010-144352 | 12/2010 |
| WO | WO 2010-144398 | 12/2010 |
| WO | WO 2011-005666 | 1/2011 |
| WO | WO 2012-088056 | 6/2012 |

OTHER PUBLICATIONS

Al-Anazi, "A Successful Methanol Treatment in a Gas-Condensate Reservoir: Field Application", Mar. 2003, Society of Petroleum Engineers Inc., pp. 1-9, SPE 80901.

Clark, "Use of Fluorochemical Surfactants in Nonaqueous Stimulation Fluids," Oct. 1980, Journal of Petroleum Chemistry, vol. 32, No. 10, pp. 1695-1697.

Crema, "Foaming of Anhydrous Methanol for Well Stimulation", Apr. 1985, Society of Petroleum Engineers Inc., 4 pages, SPE 13565.

Fahes, "Wettability Alteration to Intermediate Gas-Wetting in Gas-Condensate Reservoirs at High Temperatures", Oct. 9-12, 2005, SPE Annual Technical Conference and Exhibition, Dallas, TX, pp. 1-14. SPE 96184.

Kamath, "Laboratory Based Evaluation of Gas Well Deliverability Loss Due to Waterblocking" SPE 63161, SPE Annual Technical Conference and Exhibition, Oct. 2000, 15 pages.

Kumar, "Improving the Gas and Condensate Relative Permeability Using Chemical Treatments", May 15-17, 2006, SPE Gas Technology Symposium, Calgary, Alberta, pp. 1-9. SPE 100529.

(56) References Cited

OTHER PUBLICATIONS

Kumar, "Chemical Stimulation of Gas/Condensate Reservoirs", SPE 102669, SPE Annual Technical Conference and Exhibition, Sep. 2006, vol. 4, pp. 2688-2696.

Li, "Experimental Study of Wettability Alteration to Preferential Gas-Wetting in Porous Media and Its Effects", SPE Reservoir Evaluation & Engineering, Apr. 2000, vol. 3, No. 2, pp. 139-149.

Mahadevan, "Clean-up of Water Blocks in Low Permeability Formations", SPE 84216, SPE Annual Technical Conference and Exhibition, Oct. 2003, 8 pages.

Mahadevan, "Evaporative Clean-up of Water-Blocks in Gas Wells", SPE 94215, SPE Production and Operations Symposium, Apr. 2005, 11 pages.

Mahadevan, Capillary Wicking in Gas Wells, SPE 103229, SPE Journal, Dec. 2007, pp. 429-437.

McLeod, "The Use of Alcohol in Gas Well Stimulation", Nov. 10-11, 1966, SPE Eastern Regional Meeting, Columbus, Ohio, pp. 1-13, SPE 1663.

Noh, "Effect of Wettability on High-Velocity Coefficient in Two-Phase Gas-Liquid Flow", SPE Annual Technical Conference and Exhibition held in San Antonio, TX, Sep. 24-27, 2006, SPE Annual Technical Conference and Exhibition, Texas, pp. 1-8, SPE 102773.

Noh, "Experimental Study of Wettability Alteration for Reservoir Rock", Project 3-Gas Condensate Reservoirs Part 2, Reservoir Engineering Research Institute, Apr. 1-Jun. 30, pp. 1-7.

Panga, "Preventive Treatment for Enhancing Water Removal from Gas Reservoirs by Wettability Alteration", Mar. 11-14, 2007, 15th SPE Middle East Oil & Gas Show and Conference, Kingdom of Bahrain, pp. 1-12. SPE 105367.

Tang, "Relative Permeability Modification in Gas/Liquid Systems Through Wettability Alteration to Intermediate Gas Wetting", SPE Reservoir Evaluation and Engineering, Dec. 2002, vol. 5, No. 6, pp. 427-436.

International Search Report for PCT/US2012/021165, mailed on Aug. 24, 2012, p. 5.

European Search Report for 12 75 7897, Jun. 11, 2014, 4 pages.

The People's Republic of China Search Report for Application No. 201280005440.5, Nov. 25, 2014, 2 pages.

\* cited by examiner

METHODS FOR TREATING SILICICLASTIC HYDROCARBON-BEARING FORMATIONS WITH FLUORINATED AMINE OXIDES

CROSS REFERENCE TO RELATED APPLICATION

This application is a national stage filing under 35 U.S.C. 371 of PCT/US2012/021165, filed Jan. 13, 2012, which claims priority to U.S. Provisional Application No. 61/432,388, filed Jan. 13, 2011, the disclosure of which is incorporated by reference in its entirety herein.

BACKGROUND

In the oil and gas industry, certain surfactants (including certain fluorinated surfactants) are known as fluid additives for various downhole operations (e.g., fracturing, water-flooding, and drilling). Often, these surfactants function to decrease the surface tension of the fluid or to stabilize foamed fluids.

Some hydrocarbon and fluorochemical compounds have been used to modify the wettability of reservoir rock, which may be useful, for example, to prevent or remedy water blocking (e.g., in oil or gas wells) or liquid hydrocarbon accumulation (e.g., in gas wells) in the vicinity of the wellbore (i.e., the near wellbore region). Water blocking and liquid hydrocarbon accumulation may result from natural phenomena (e.g., water-bearing geological zones or condensate banking) and/or operations conducted on the well (e.g., using aqueous or hydrocarbon fluids). Water blocking and condensate banking in the near wellbore region of a hydrocarbon-bearing geological formation can inhibit or stop production of hydrocarbons from the well and hence are typically not desirable. Not all hydrocarbon and fluorochemical compounds, however, provide the desired wettability modification. And some of these compounds modify the wettability of siliciclastic hydrocarbon-bearing formations but not carbonate formations, or vice versa. Hence, there is a continuing need for alternative and/or improved techniques for increasing the productivity of oil and/or gas wells that have brine and/or two phases of hydrocarbons in a near wellbore region of a hydrocarbon-bearing geological formation.

SUMMARY

The methods described herein may be useful in hydrocarbon-bearing formations having at least one of brine (e.g., connate brine and/or water blocking) or two phases of hydrocarbons present in the near wellbore region, (e.g., in gas wells having retrograde condensate and oil wells having black oil or volatile oil), for providing an increase in permeability of at least one of gas, oil, condensate, or brine. Treatment of an oil and/or gas well that has brine and/or two phases of hydrocarbons in the near wellbore region using the methods disclosed herein may increase the productivity of the well. Although not wishing to be bound by theory, it is believed that the fluorinated amine oxides disclosed herein generally at least one of adsorb to, chemisorb onto, or react with siliciclastic, hydrocarbon-bearing formations under downhole conditions and modify the wetting properties of the rock in the formation to facilitate the removal of hydrocarbons and/or brine.

In one aspect, the present disclosure provides a method of treating a siliciclastic, hydrocarbon-bearing formation, the method comprising contacting the siliciclastic, hydrocarbon-bearing formation with a treatment composition comprising solvent and a fluorinated amine oxide, wherein the fluorinated amine oxide does not have polymeric repeating units comprising amine oxide groups. In some of these embodiments, the fluorinated amine oxide is non-polymeric.

In another aspect, the present disclosure provides a method of treating a siliciclastic, hydrocarbon-bearing formation, the method comprising contacting the siliciclastic, hydrocarbon-bearing formation with a treatment composition comprising solvent and a fluorinated amine oxide, wherein the siliciclastic, hydrocarbon-bearing formation has at least one fracture, and the fracture has a plurality of proppants therein. In some embodiments of the foregoing aspects, the fluorinated amine oxide does not have polymeric repeating units comprising an amine oxide. In some of these embodiments, the fluorinated amine oxide is non-polymeric. In other embodiments of the foregoing aspects, the fluorinated amine oxide is polymeric.

In another aspect, the present disclosure provides a siliciclastic, hydrocarbon-bearing formation treated according to any of the aforementioned methods.

Exemplary siliciclastic, hydrocarbon-bearing formations include shale, conglomerate, diatomite, sand, and sandstone formations. In some embodiments of the foregoing aspects, at least one of shale, conglomerate, diatomite, sand, or sandstone forms at least a portion (e.g., at least 50, 60, 75, or 90 percent by weight) of the siliclastic, hydrocarbon-bearing formation. In some embodiments of the foregoing aspects, the siliciclastic, hydrocarbon-bearing formation comprises sandstone (e.g., at least 50, 60, 75, or 90 percent by weight sandstone).

In some embodiments of the foregoing aspects, the fluorinated amine oxide is represented by formula $Rf$-$Q$-$N(R)_2$—$O$, wherein $Rf$ is independently fluoroalkyl having up to 10 carbon atoms or a polyfluoropolyether group;

$Q$ is —$SO_2$—$N(R')$—$W$—, —$C(O)$—$N(R')$—$W$—, alkylene, arylalkylene, or arylene, wherein alkylene and arylalkylene are each optionally interrupted by —$O$—, —$S$—, —$SO_2$—, or —$C(O)$— and optionally substituted by hydroxyl;

$R'$ is hydrogen, alkyl having up to six carbon atoms, or aryl;

$W$ is alkylene, arylalkylene, or arylene, wherein alkylene and arylalkylene are each optionally interrupted by —$O$— or —$S$— and optionally substituted by hydroxyl; and each $R$ is independently hydrogen, alkyl, or aryl, wherein alkyl may optionally be interrupted by —$O$— or substituted with hydroxyl or aryl, or two $R$ groups taken together with the N atom to which they are attached can form a heterocyclic ring having up to six carbon atoms and optionally containing —$O$— or —$S$—.

In some embodiments of the foregoing aspects, the fluorinated amine oxide is represented by formula:

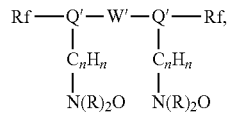

wherein $Rf$ is independently fluoroalkyl having up to 10 carbon atoms or a polyfluoropolyether group;

Q' is —SO$_2$N(—)(—), —(CH$_2$)$_p$CH(O—)(—), or —(CH$_2$)$_p$—CH(O—)(CH$_2$)$_p$O—, where p is an integer of 1 to 11;

W' is alkylene, arylalkylene, or arylene, wherein alkylene and arylalkylene are each optionally interrupted by —O— or —S— and optionally substituted by hydroxyl;

each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—; and each n is independently 0 to 11.

In some embodiments (e.g., embodiments wherein the siliciclastic formation is fractured), the fluorinated amine oxide is polymeric and comprises:

a first divalent unit represented by formula

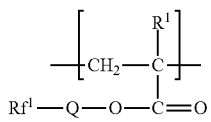

and a second divalent unit represented by formula

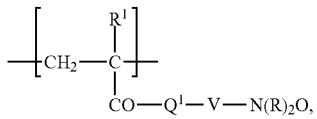

wherein each Rf$^1$ is independently fluoroalkyl having up to 10 carbon atoms or a polyfluoropolyether group;

each Q is independently —SO$_2$—N(R)—W—, —C(O)—N(R')—W—, alkylene, arylalkylene, or arylene, wherein alkylene and arylalkylene are each optionally interrupted by —O—, —S—, —SO$_2$—, or —C(O)— and optionally substituted by hydroxyl;

each W is independently alkylene, arylalkylene, or arylene, wherein alkylene and arylalkylene are each optionally interrupted by —O— or —S— and optionally substituted by hydroxyl;

each V is independently alkylene, arylalkylene, or arylene, wherein alkylene and arylalkylene are each optionally interrupted by —O— or —S— and optionally substituted by hydroxyl;

each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—;

R' is hydrogen, alkyl having up to 6 carbon atoms, or aryl;

each R$^1$ is independently hydrogen or methyl; and each Q$^1$ is independently —O—, —S—, or —N(R")—, wherein R" is hydrogen or alkyl having up to 6 carbon atoms.

In some embodiments of the foregoing methods, the solvent comprises at least one of water, a monohydroxy alcohol, an ether, a ketone, a glycol, a glycol ether, or supercritical carbon dioxide.

In some embodiments of the foregoing methods, the hydrocarbon-bearing formation is a gas producing formation penetrated by a wellbore, and a region near the wellbore is contacted with the treatment composition. In some of these embodiments, the method further comprises obtaining gas from the wellbore after contacting the hydrocarbon-bearing formation with the composition. The region near the wellbore (i.e., near wellbore region) includes a region within about 25 feet (in some embodiments, 20, 15, or 10 feet) of the wellbore. In some embodiments, before contacting the hydrocarbon-bearing formation with the treatment composition, the hydrocarbon-bearing formation has retrograde gas condensate, black oil, or volatile oil, and the hydrocarbon-bearing formation has an increase in at least gas permeability after it is contacted with the treatment composition.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "at least one of" followed by a list refers to any one of the items in the list and any combination of two or more items in the list.

The term "brine" refers to water having at least one dissolved electrolyte salt therein (e.g., sodium chloride, calcium chloride, strontium chloride, magnesium chloride, potassium chloride, ferric chloride, ferrous chloride, and hydrates thereof) at any nonzero concentration (in some embodiments, less than 1000 parts per million by weight (ppm), or greater than 1000 ppm, greater than 10,000 ppm, greater than 20,000 ppm, 30,000 ppm, 40,000 ppm, 50,000 ppm, 100,000 ppm, 150,000 ppm, or even greater than 200,000 ppm).

The term "hydrocarbon-bearing formation" includes both hydrocarbon-bearing formations in the field (i.e., subterranean hydrocarbon-bearing formations) and portions of such hydrocarbon-bearing formations (e.g., core samples).

The term "productivity" as applied to a well refers to the capacity of a well to produce hydrocarbons (i.e., the ratio of the hydrocarbon flow rate to the pressure drop, where the pressure drop is the difference between the average reservoir pressure and the flowing bottom hole well pressure (i.e., flow per unit of driving force)).

The term "contacting" includes placing a composition within a hydrocarbon-bearing formation using any suitable manner known in the art (e.g., pumping, injecting, pouring, releasing, displacing, spotting, or circulating the treatment composition into a well, wellbore, or hydrocarbon-bearing formation).

"Alkyl group" and the prefix "alk-" are inclusive of both straight chain and branched chain groups and of cyclic groups. Unless otherwise specified, alkyl groups herein have up to 20 carbon atoms. Cyclic groups can be monocyclic or polycyclic and, in some embodiments, have from 3 to 10 ring carbon atoms. "Alkylene" is the divalent form of "alkyl".

The term "fluoroalkyl" includes linear, branched, and/or cyclic alkyl groups in which all C—H bonds are replaced by C—F bonds as well as groups in which hydrogen or chlorine atoms are present instead of fluorine atoms provided that up to one atom of either hydrogen or chlorine is present for every two carbon atoms. In some embodiments of fluoroalkyl groups, when at least one hydrogen or chlorine is present, the fluoroalkyl group includes at least one trifluoromethyl group. The term "perfluoroalkyl group" includes linear, branched, and/or cyclic alkyl groups in which all C—H bonds are replaced by C—F bonds. The term "interrupted by up to 5 ether groups" refers to having fluoroalkyl on both sides of the ether group.

The term "aryl" as used herein includes carbocyclic aromatic rings or ring systems, for example, having 1, 2, or 3 rings, optionally containing at least one heteroatom (e.g., O, S, or N) in the ring, and optionally substituted by up to five substituents including one or more alkyl groups having up to 4 carbon atoms (e.g., methyl or ethyl), alkoxy having up to 4 carbon atoms, halo (i.e., fluoro, chloro, bromo or iodo), hydroxy, or nitro groups. Examples of aryl groups include phenyl, naphthyl, biphenyl, fluorenyl as well as furyl, thienyl, oxazolyl, and thiazolyl.

"Arylene" is the divalent form of the "aryl" groups defined above.

"Alkylarylene" refers to an "arylene" moiety to which an alkyl group is attached.

"Arylalkylene" refers to an "alkylene" moiety to which an aryl group is attached.

The term "solvent" refers to a homogeneous liquid material, which may be a single compound or a combination of compounds and which may or may not include water, that is capable of at least partially dissolving a fluorinated amine oxide disclosed herein at 25° C.

The term "polymer" refers to a molecule having a structure which essentially includes the multiple repetition of units derived from molecules of low relative molecular mass. The term "polymer" encompasses oligomers. Polymers may have repeating units from the same monomer or a combination of monomers. The term "non-polymeric" refers to a molecule having a structure that does not include the multiple repetition of units derived from molecules of low relative molecular mass. Non-polymeric compounds may also be referred to as "small molecules".

The term "precipitate" means to separate from solution and remain separated under the conditions of the treatment method (e.g., in the presence of the brine and at the temperature of the hydrocarbon-bearing formation).

All numerical ranges are inclusive of their endpoints and non-integral values between the endpoints unless otherwise stated.

BRIEF DESCRIPTION OF THE DRAWINGS

For a more complete understanding of the features and advantages of the present disclosure, reference is now made to the detailed description along with the accompanying figures and in which.

DETAILED DESCRIPTION

Figure 1:
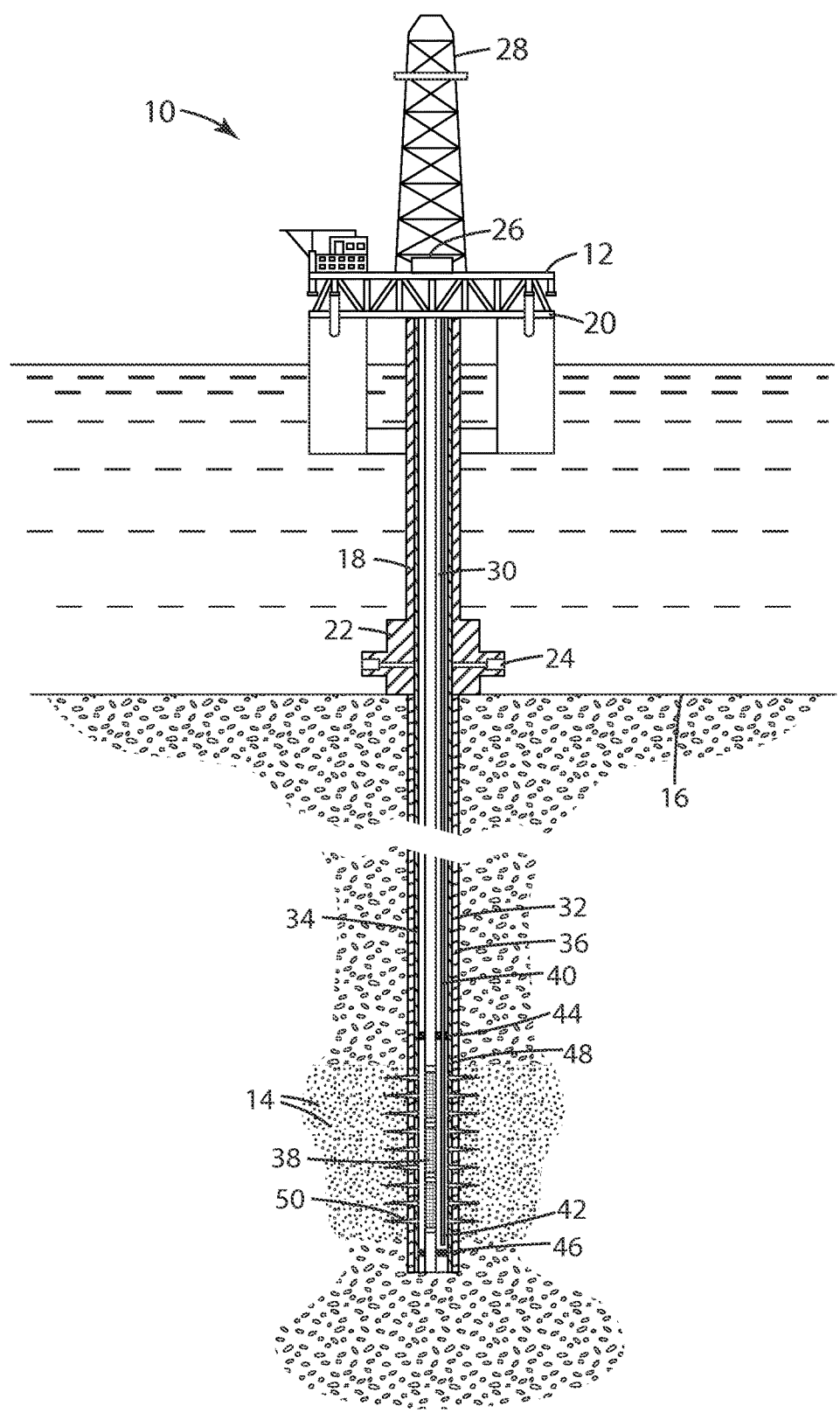
FIG. 1 is a schematic illustration of an exemplary embodiment of an offshore oil platform operating an apparatus for progressively treating a near wellbore region according to the present disclosure.

Methods according to the present disclosure include contacting a siliciclastic, hydrocarbon-bearing formation with a treatment composition comprising solvent and a fluorinated amine oxide. In some embodiments, the fluorinated amine oxide is represented by formula Rf-Q-N(R)$_2$—O,

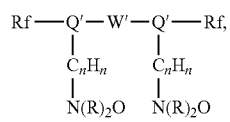

or combinations thereof. In some embodiments, the fluorinated amine oxide is a compound comprising:

at least one (e.g., at least 2, 5, or 10, for example in a range from 1 to 100 or 1 to 20) first divalent unit represented by formula

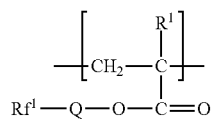

and at least one (e.g., at least 2, 5, or 10, for example in a range from 1 to 100 or 1 to 20) second divalent unit represented by formula

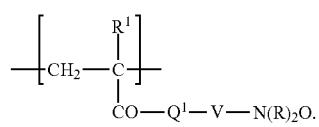

In any of the above embodiments having an Rf group, Rf may be a fluoroalkyl group having up to 10 carbon atoms (e.g., up to 8, 6, or 4 carbon atoms, for example, in a range from 2 to 10, 4 to 8, or 2 to 6 carbon atoms). Exemplary Rf groups include trifluoromethyl, perfluoroethyl, 1,1,2,2-tetrafluoroethyl, 2-chlorotetrafluoroethyl, perfluoro-n-propyl, perfluoroisopropyl, perfluoro-n-butyl, 1,1,2,3,3,3-hexafluoropropyl, perfluoroisobutyl, perfluoro-sec-butyl, or perfluoro-tert-butyl, perfluoro-n-pentyl, pefluoroisopentyl, perfluorohexyl, perfluoroheptyl, or perfluorooctyl. In some embodiments, Rf is perfluorobutyl (e.g., perfluoro-n-butyl, perfluoroisobutyl, or perfluoro-sec-butyl). In some embodiments, Rf is perfluoropropyl (e.g., perfluoro-n-propyl). Rf may be a mixture of fluoroalkyl groups.

In some embodiments, Rf is a polyfluoropolyether group. The term "polyfluoropolyether" refers to a compound or group having at least 3 (in some embodiments, at least 4, 5, 6, 7, 8, 9, 10, 11, 12, 13, 14, 15, 16, 17, 18, 19, or even 20) carbon atoms and at least 3 (in some embodiments, at least 4, 5, 6, 7, or even 8) ether linkages, wherein the hydrogen atoms on the carbon atoms are replaced with fluorine atoms. In some embodiments, Rf has up to 100, 110, 120, 130, 140, 150, or even 160 carbon atoms and up to 25, 30, 35, 40, 45, 50, 55, or even 60 ether linkages. In these embodiments, the fluorinated amine oxide may be considered to be polymeric but not having polymeric repeating units comprising amine oxide groups.

The polyfluoropolyether group Rf can be linear, branched, cyclic, or combinations thereof and can be saturated or unsaturated. Polyfluoropolyether groups include those in which fluorine or chlorine atoms are present instead of fluorine atoms provided that up to one atom of either hydrogen or chlorine is present for every two carbon atoms. In some embodiments, the polyfluoropolyether group is a perfluoropolyether group (i.e., all of the hydrogen atoms on the carbon atoms are replaced with fluorine atoms). Exemplary perfluoropolyethers include perfluorinated repeating units represented by at least one of —($C_dF_{2d}$)—, —($C_dF_{2d}O$)—, —(CF(L'))—, —(CF(L')O)—, —(CF(L')$C_dF_{2d}O$)—, —($C_dF_{2d}CF(L')O$)—, or —($CF_2CF(L')O$)—. In these repeating units, d is typically an integer of 1 to 10. In some embodiments, d is an integer of 1 to 8, 1 to 6, 1 to 4, or 1 to 3. The L' group can be a perfluoroalkyl group optionally interrupted by at least one ether linkage or a perfluoroalkoxy group, each of which may be linear, branched, cyclic, or a combination thereof. The L' group typically has up to 12 (in some embodiments, up to 10, 8, 6, 4, 3, 2, or 1) carbon atoms. In some embodiments, the L' group can have up to 4 (in some embodiments, up to 3, 2, or 1) oxygen atoms; in some embodiments L' has no oxygen atoms. In these perfluoropolyether structures, different repeating units can be combined in a block or random arrangement to form the Rf group. Rf may be a mixture of polyfluoropolyether groups.

In some embodiments, Rf is represented by formula $R_f^a$—O—($R_f^b$—O—)$_z'$($R_f^c$)—, wherein $R_f^a$ is a perfluoroalkyl having 1 to 10 (in some embodiments, 1 to 6, 1 to 4, 2 to 4, or 3) carbon atoms; each $R_f^b$ is independently a perfluoroalkylene having 1 to 4 (i.e., 1, 2, 3, or 4) carbon atoms; $R_f^c$ is a perfluoroalkylene having 1 to 6 (in some embodiments, 1 to 4 or 2 to 4) carbon atoms; and z' is in a range from 2 to 50 (in some embodiments, 2 to 25, 2 to 20, 3 to 20, 3 to 15, 5 to 15, 6 to 10, or 6 to 8). Representative $R_f^a$ groups include $CF_3$—, $CF_3CF_2$—, $CF_3CF_2CF_2$—, $CF_3CF(CF_3)$—, $CF_3CF(CF_3)CF_2$—, $CF_3CF_2CF_2CF_2$—, $CF_3CF_2CF(CF_3)$—, $CF_3CF_2CF(CF_3)CF_2$—, and $CF_3CF(CF_3)CF_2CF_2$—. In some embodiments, $R_f^a$ is $CF_3CF_2CF_2$—. Representative $R_f^b$ groups include —$CF_2$—, —$CF(CF_3)$—, —$CF_2CF_2$—, —$CF(CF_3)CF_2$—, —$CF_2CF_2CF_2$—, —$CF(CF_3)CF_2CF_2$—, —$CF_2CF_2CF_2CF_2$—, and —$CF_2C(CF_3)_2$—. Representative $R_f^c$ groups include —$CF_2$—, —$CF(CF_3)$—, —$CF_2CF_2$—, —$CF_2CF_2CF_2$—, and —$CF(CF_3)CF_2$—. In some embodiments, $R_f^c$ is —$CF(CF_3)$—.

In some embodiments, ($R_f^b$—O—)$_{z'}$ is represented by —[$CF_2O$]$_i$[$CF_2CF_2O$]$_j$—, —[$CF_2O$]$_i$[$CF(CF_3)CF_2O$]$_j$—, —[$CF_2O$]$_i$[$CF_2CF_2CF_2O$]$_j$—, —[$CF_2CF_2O$]$_i$[$CF_2O$]$_j$—, —[$CF_2CF_2O$]$_i$[$CF(CF_3)CF_2O$]$_j$—, —[$CF_2CF_2O$]$_i$[$CF_2CF_2CF_2O$]$_j$—, —[$CF_2CF_2CF_2O$]$_i$[$CF_2CF(CF_3)O$]$_j$—, and [$CF_2CF_2CF_2O$]$_i$[$CF(CF_3)CF_2O$]$_j$—, wherein i+j is an integer of at least 3 (in some embodiments, at least 4, 5, or 6).

In some embodiments, Rf is selected from the group consisting of $C_3F_7O(CF(CF_3)CF_2O)_xCF(CF_3)$—, $C_3F_7O(CF_2CF_2CF_2O)_xCF_2CF_2$—, or $CF_3O(C_2F_4O)_yCF_2$—, wherein x has an average value in a range from 3 to 50 (in some embodiments, 3 to 25, 3 to 15, 3 to 10, 4 to 10, or 4 to 7), and wherein y has an average value in a range from 6 to 50 (in some embodiments, 6 to 25, 6 to 15, 6 to 10, 7 to 10, or 8 to 10). In some of these embodiments, Rf is $C_3F_7O(CF(CF_3)CF_2O)_xCF(CF_3)$—, wherein x has an average value in a range from 4 to 7. In some embodiments, Rf is selected from the group consisting of $CF_3O(CF_2O)_{x'}(C_2F_4O)_{y'}CF_2$— and $F(CF_2)_3$—O—$(C_4F_8O)_{z''}(CF_2)_3$—, wherein x', y', and z" each independently has an average value in a range from 3 to 50 (in some embodiments, 3 to 25, 3 to 15, 3 to 10, or even 4 to 10).

In some embodiments wherein Rf is a polyfluoropolyether, Rf has a weight average molecular weight of at least 750 (in some embodiments at least 850 or even 1000) grams per mole. In some embodiments, Rf has a weight average molecular weight of up to 6000 (in some embodiments, 5000 or even 4000) grams per mole. In some embodiments, Rf has a weight average molecular weight in a range from 750 grams per mole to 5000 grams per mole. Weight average molecular weights can be measured, for example, by gel permeation chromatography (i.e., size exclusion chromatography) using techniques known in the art.

In some embodiments, Rf is selected from the group consisting of:

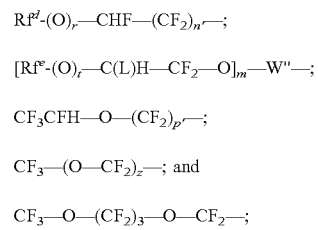

wherein
$Rf^d$ and $Rf^e$ independently represent a partially or fully fluorinated alkyl group having from 1 to 10 carbon atoms and optionally interrupted with at least one oxygen atom;
L is selected from the group consisting of F and $CF_3$;
W" is selected from the group consisting of alkylene and arylene;
r is 0 or 1, wherein when r is 0, then $Rf^d$ is interrupted with at least one oxygen atom;
t is 0 or 1;
m is 1, 2, or 3;
n' is 0 or 1;
each p' is independently a number from 1 to 6; and
z is a number from 2 to 7.

In some of these embodiments, Rf has a molecular weight of up to 600 grams per mole (in some embodiments, up to 500, 400, or even up to 300 grams per mole). $Rf^d$ and $Rf^e$ independently represent a partially or fully florinated alkyl group having from 1 to 10 carbon atoms and optionally interrupted with at least one oxygen atom. $Rf^d$ and $Rf^e$ include linear and branched alkyl groups. In some embodiments, $Rf^d$ and/or $Rf^e$ is linear. In some embodiments, $Rf^d$ and $Rf^e$ independently represent a fully fluorinated alkyl group having up to 6 (in some embodiments, 5, 4, 3, 2, or 1) carbon atoms. In some embodiments, $Rf^d$ and $Rf^e$ independently represent a fully fluorinated alkyl group interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms. In some embodiments, $Rf^d$ and $Rf^e$ independently represent a partially fluorinated alkyl group having up to 6 (in some embodiments, 5, 4, 3, 2, or 1) carbon atoms and up to 2 hydrogen atoms. In some embodiments, $Rf^d$ and $Rf^e$ independently represent a partially fluorinated alkyl group having up 2 hydrogen atoms interrupted with at least one oxygen atom, of which the alkyl groups between oxygen atoms have up to 6 (in some embodiments, 5, 4, 3, 2, or 1) carbon atoms, and wherein the terminal alkyl group has up to 6 (in some embodiments, 5, 4, 3, 2, or 1) carbon atoms.

In some embodiments of Rf, $Rf^d$ and $Rf^e$ are independently represented by formula

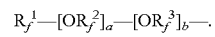

$R_f^1$ is a perfluorinated alkyl group having from 1 to 6 (in some embodiments, 1 to 4) carbon atoms. $R_f^2$ and $R_f^3$ are each independently perfluorinated alkylene having from 1 to 4 carbon atoms. "a" and b are each independently a number having a value from 0 to 4, and the sum of "a" and b is at least 1. In some of these embodiments, t is 1, and r is 1.

In some embodiments of Rf, $Rf^d$ and $Rf^e$ are independently represented by formula

$R_f^4$—[$OR_f^5$]$_{a'}$—[$OR_f^6$]$_{b'}$—O—$CF_2$—.

$R_f^4$ is a perfluorinated alkyl group having from 1 to 6 (in some embodiments, 1 to 4) carbon atoms. $R_f^5$ and $R_f^6$ are each independently perfluorinated alkylene having from 1 to 4 carbon atoms. a' and b' are each independently numbers having a value from 0 to 4. In some of these embodiments, t is 0, and r is 0.

In some embodiments of Rf, $Rf^d$ and $Rf^e$ are independently represented by formula $R_f^7$—$(OCF_2)_{p'}$—, wherein p' is an integer of 1 to 6 (in some embodiments, 1 to 4), and $R_f^7$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In some embodiments of Rf, $Rf^d$ and $Rf^e$ are independently represented by formula $R_f^8$—O—$(CF_2)_{p'}$—, wherein p' is a number from 1 to 6 (in some embodiments, 1 to 4) and $R_f^8$ is selected from the group consisting of a partially fluorinated alkyl group having 1, 2, 3, 4, 5, or 6 carbon atoms and 1 or 2 hydrogen atoms and a fully fluorinated alkyl group having 1, 2, 3 or 4 carbon atoms.

In some embodiments of Rf, L is selected from the group consisting of F and $CF_3$. In some embodiments, L is F. In other embodiments, L is $CF_3$.

In some embodiments of Rf, W" is selected from the group consisting of alkylene and arylene. Alkylene includes linear, branched, and cyclic alkylene groups having from 1 to 10 (in some embodiments, 1 to 4) carbon atoms. In some embodiments, W" is methylene. In some embodiments, W" is ethylene. Arylene includes groups having 1 or 2 aromatic rings, optionally having at least one heteroatom (e.g., N, O, and S) in the ring, and optionally substituted with at least one alkyl group or halogen atom. In some embodiments, W" is phenylene.

In some embodiments of Rf, t is 0 or 1. In some embodiments, t is 1. In some embodiments, t is 0. In embodiments wherein t is 0, Rf is typically interrupted by at least one oxygen atom.

In some embodiments of Rf, m is 1, 2, or 3. In some embodiments, m is 1.

In some embodiments of Rf, n' is 0 or 1. In some embodiments, n' is 0. In some embodiments, n' is 1.

In some embodiments of Rf, p' is a number from 1 to 6 (i.e., 1, 2, 3, 4, 5, or 6). In some embodiments, p' is 1, 2, 5, or 6. In some embodiments, p' is 3. In some embodiments, p' is 1 or 2. In some embodiments, p' is 5 or 6.

In some embodiments of Rf, z is a number from 2 to 7 (i.e., 2, 3, 4, 5, 6, or 7). In some embodiments, z is an integer from 2 to 6, 2 to 5, 2 to 4, or 3 to 4.

In some embodiments, fluorinated amine oxides disclosed herein have an Rf group represented by $CF_3CFH$—O—$(CF_2)_{p'}$—. In some of these embodiments Rf is selected from the group consisting of $CF_3CFH$—O—$(CF_2)_3$— and $CF_3CFH$—O—$(CF_2)_5$—.

In some embodiments, fluorinated amine oxides disclosed herein have an Rf group represented by $CF_3$—$(O$—$CF_2)_z$—. In some of these embodiments, z is a number from 2 to 6, 2 to 5, 2 to 4, 3 to 5, or 3 to 4.

In some embodiments, fluorinated amine oxides disclosed herein have an Rf represented by $CF_3$—O—$(CF_2)_3$—O—$CF_2$—. In some embodiments, fluorinated amine oxides disclosed herein have an Rf selected from the group consisting of $CF_3$—O—$CF_2CF_2$—$CF_2$—O—$CHF$—, $CF_3$—O—$CF_2$—$CF_2$—$CF_2$—O—$CF_2$—$CHF$—, $CF_3$—O—$CF_2$—$CF_2$—$CF_2$—O—$CHF$—$CF_2$—, and $CF_3$—O—$CF_2$—$CF_2$—$CF_2$—O—$CF_2$—$CHF$—$CF_2$—.

Other useful Rf structures include partially fluorinated Rf groups disclosed, for example, in PCT International Pub. No. WO 2008/154345 A1 (Dams et al.), pages 8 to 10, the disclosure of which is incorporated herein by reference.

For embodiments of fluorinated amine oxides comprising first and second divalent units, each $Rf^1$ is independently defined as in any of the embodiments of Rf above.

In any of the aforementioned embodiments containing a Q group, each Q is independently —$SO_2$—N(R')—W—, —C(O)—N(R')—W—, alkylene, arylalkylene, or arylene, wherein alkylene and arylalkylene are each optionally interrupted by —O—, —S—, —$SO_2$—, or —C(O)— and optionally substituted by hydroxyl; wherein R' is hydrogen, an alkyl group having up to 6 carbon atoms, or aryl. The term "interrupted by —O—, —S—, —$SO_2$—, or —C(O)—" refers to having a portion of the alkylene group on either side of the —O—, —S—, —$SO_2$—, or —C(O)—. In some embodiments, Q is —$SO_2$—N(R')—W— or alkylene having up to four carbon atoms. In some embodiments, Q is —$SO_2$—N(R')—W—. In some embodiments, R' is hydrogen or alkyl having up to four carbon atoms (e.g., methyl or ethyl). In some embodiments, Q is —$CH_2$—$CH_2$—. In some embodiments, Q is —CH(OH)—$CH_2$—.

In any of the aforementioned embodiments containing a W group, each W is independently alkylene, arylalkylene, or arylene, wherein alkylene and arylalkylene are each optionally interrupted by —O— or —S— and optionally substituted by hydroxyl. In some of these embodiments, W is alkylene (e.g., having up to 6, 4, or 3 carbon atoms).

In any of the aforementioned embodiments containing a V group, each V is independently alkylene, arylalkylene, or arylene, wherein alkylene and arylalkylene are each optionally interrupted by —O— or —S— and optionally substituted by hydroxyl. In some of these embodiments, V is alkylene (e.g., having up to 6, 4, or 3 carbon atoms).

In any of the aforementioned embodiments containing a R group, each R is independently hydrogen, alkyl, or aryl, wherein alkyl may optionally be interrupted by —O— or substituted with hydroxyl or aryl, or two R groups taken together with the N atom to which they are attached can form a heterocyclic ring having 5 to 7 carbon atoms and optionally containing —O— or —S—. In some embodiments, each R is independently hydrogen or alkyl having up to 4 carbon atoms. In some embodiments, each R is independently alkyl having up to four carbon atoms (e.g., methyl or ethyl). Exemplary heterocyclic rings having 5 to 7 carbon atoms include pyrrolium, pyrimidinium, isoxazolium, oxazolium, thiazolium, isothiazolium, pyridinium, pyrrolidinium, piperidinium, morpholinium, and azepinium).

In any of the aforementioned embodiments containing a R' group, each R' is independently hydrogen or methyl.

In any of the aforementioned embodiments containing a $Q^1$ group, each $Q^1$ is independently —O—, —S—, or —N(R")—, wherein R" is hydrogen or alkyl having up to 6 carbon atoms. In some embodiments, $Q^1$ is —O—.

In any of the aforementioned embodiments containing a Q' group, each Q' is independently —$SO_2N(—)(—)$, —$(CH_2)_pCH(O—)(—)$, or —$(CH_2)_p$—$CH(O—)$ $(CH_2)_pO$—, where p is a number from 1 to 11. In some embodiments, p is from 1 to 6 or 1 to 4. In some embodiments, Q' is —$SO_2N(—)(—)$. In these variations of Q', the bond on the left side of the group is attached to the Rf group, and the other two bonds are attached to the W' and $C_nH_n$ groups.

In any of the aforementioned embodiments containing a W group, each W is alkylene, arylalkylene, or arylene, wherein alkylene and arylalkylene are each optionally interrupted by —O— or —S— and optionally substituted by hydroxyl. In some embodiments, W' is alkylene that is optionally interrupted by —O—. In some embodiments, W' is alkylene having up to 4 carbon atoms.

In any of the aforementioned embodiments containing an n group, each n is independently 0 to 11. In some embodiments, each n is independently 1 to 11. In some embodiments, each n is independently 1 to 8, 1 to 6, or 1 to 4.

Fluorinated amine oxides can be prepared, for example, using conventional techniques. For example, fluorinated sulfonyl fluorides (e.g., perfluoro-1-butanesulfonyl fluoride, which is available from Sigma-Aldrich, St. Louis, Mo., and perfluoro-1-hexanesulfonyl fluoride), fluorinated carboxylic acids or their derivatives, and fluorinated epoxides can be treated with an amine having formula $NH_2$—W—$NR_2$ (e.g., 3-(dimethylamino)propylamine) in a first step to provide an amino-functionalized sulfonamide, carboxamide, or hydroxyl compound which can then be treated with an oxidizing agent (e.g., hydrogen peroxide or m-chloroperoxybenzoic acid) using conventional techniques. Some fluorinated carboxylic acids and fluorinated acid fluorides that may be useful for reaction with an amine having formula $NH_2$—W—$NR_2$ are commercially available (e.g., carboxylic acids of formula $CF_3$—[O—$CF_2$]$_{1-3}$C(O)OH, available, for example, from Anles Ltd., St. Petersburg, Russia, and acid fluorides of formulas $C_2F_5$—O—$(CF_2)_2$—C(O)F, $C_3F_7$—O—$(CF_2)_2$—C(O)F and $CF_3CF_2$—O—$CF_2CF_2$—O—$CF_2$C(O)F, available, for example, from Exfluor, Round Rock, Tex.). In some embodiments of the methods and the hydrocarbon-bearing formations disclosed herein, Rf is a perfluorinated polyether group of formula: $CF_3CF_2CF_2$—O—[CF($CF_3$)$CF_2$O]$_x$—CF($CF_3$)—, wherein x is as defined above. Fluorinated acids of this type can be prepared by oligomerization of hexafluoropropylene oxide to provide a perfluoropolyether carbonyl fluoride. Several fluorinated epoxides are available, for example, from Sigma-Aldrich, St. Louis, Mo., and 1H, 1H, 2H, 3H, 3H-perfluorononylene-1,2-oxide and 1H, 1H, 2H, 3H, 3H-perfluoroheptylene-1,2-oxide are available from ABCR GmbH & Co., Germany.

Fluorinated carboxylic acids that are useful for preparing partially fluorinated amine oxides disclosed herein can also be prepared, for example, starting from fluorinated ether olefins represented by formula $Rf^e$—(O)$_t$—CF=$CF_2$, wherein $Rf^e$ represents a partially or fully fluorinated alkyl group having from 1 to 10 carbon atoms and optionally interrupted with at least one oxygen atom, and t is 0 or 1, with the proviso that when t is 0, then $Rf^e$ is interrupted with at least one oxygen atom. Conditions for the preparation of compounds of formula $Rf^e$—(O)$_t$—CHF—$CF_2$—C(O)OH, $CF_3$—$(CF_2)_2$—O—$CF_2$—C(O)—$CH_3$ and $CF_3$—O—$(CF_2)_3$—O—$CF_2$—C(O)—$CH_3$, are described, for example, in U. S. Pat. App. No. 2007/0015864 (Hintzer et al.). Fluorinated carboxylic acids represented by formula $CF_3CFH$—O—$(CF_2)_{p'}$—C(O)OH, wherein p' is 1 to 6, and their derivatives can be prepared, for example, by decarbonylation of difunctional perfluorinated acid fluoride according to the reaction:

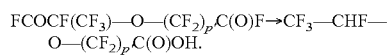

using conditions, e.g., in U.S. Pat. No. 3,555,100 (Garth et al.).

Fluorinated amine oxides represented by formula:

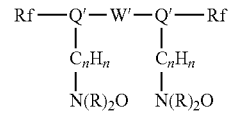

can be prepared, for example, using the methods described in U.S. Pat. No. 7,547,732 (Moore et al.). Such compounds would be considered by a person having ordinary skill in the art to not have polymeric repeating units comprising amine oxide groups. Such compounds would typically be considered non-polymeric.

Compounds comprising first and second divalent units described above can also be prepared by conventional techniques. In some embodiments, the compound comprising first and second divalent units is a polymer having a weight average molecular weight in a range from 1,000 to 100,000, from 2,000 to 100,000, from 3,500 to 100,000, or from 10,000 to 75,000 grams per mole or in a range from 1,000 to 20,000, or from 2,000 to 10,000 grams per mole. Weight average molecular weights can be measured, for example, by gel permeation chromatography (i.e., size exclusion chromatography) using techniques known in the art. It will be appreciated by one skilled in the art that such polymers can exist as a mixture of compositions and molecular weights. In some embodiments, the first divalent units are present in a range from 25 to 99 (in some embodiments, from 35 to 99, from 50 to 99, from 60 to 98, from 75 to 97, or even from 85 to 97) based on the total weight of the compound (e.g., polymer). A first divalent unit is typically introduced into fluorinated amine oxides useful for practicing the present disclosure by reacting a monomer represented by formula $CH_2$=C($R^1$)—C(O)—O-Q-$Rf^1$, for example, under free-radical conditions. Fluorochemical monomers represented by this formula and methods for the preparation thereof are known in the art (see, e.g., U.S. Pat. No. 2,803,615 (Ahlbrecht et al.), the disclosure of which is incorporated herein by reference). Further examples of such compounds include acrylates or methacrylates derived from fluorochemical telomer alcohols, acrylates or methacrylates derived from fluorochemical carboxylic acids or esters, and perfluoroalkyl acrylates or methacrylates as disclosed in U.S. Pat. No. 5,852,148 (Behr et al.), the disclosure of which is incorporated herein by reference. Fluorochemical carboxylic acids or esters containing polyfluoropolyether groups can be converted into acrylates or methacrylates using the techniques described in US Patent Application No. 2007/0243389 (Audenaert et al.), sections (0083) to (0085) and (0092) to (0094), incorporated herein by reference.

Some useful monomers represented by formula $CH_2$=C($R^1$)—C(O)—O-Q-$Rf^1$ include $C_4F_9SO_2N(CH_3)C_2H_4OC(O)CH$=$CH_2$, $C_4F_9SO_2N(CH_3)C_2H_4OC(O)C(CH3)$=$CH_2$, $C_5F_{11}SO_2N(C_2H_5)C_2H_4OC(O)CH$=$CH_2$, $C_6F_{13}SO_2N(C_2H_5)C_2H_4OC(O)C(CH_3)$=$CH_2$, $C_3F_7SO_2N(C_4H_9)C_2H_4OC(O)CH$=$CH_2$, $C_4F_9CH_2CH_2OC(O)CH$=$CH_2$, $C_5F_{11}CH_2OC(O)CH$=$CH_2$, $C_6F_{13}CH_2CH_2OC(O)CH$=$CH_2$, $CF_3(CF_2)_2CH_2OC(O)CH$=$CH_2$, $CF_3(CF_2)_2CH_2OC(O)C(CH_3)$=$CH_2$, $CF_3(CF_2)_3CH_2OC(O)C(CH_3)$=$CH_2$, $CF_3(CF_2)_3CH_2OC(O)CH$=$CH_2$, $CF_3(CF_2)_3S(O)_2N(R^a)$—$(CH_2)_2$—OC(O)CH$=$CH_2$, $CF_3(CF_2)_3S(O)_2N(R^a)$—$(CH_2)_2$—OC(O)C(CH_3)$=$CH_2$, $CF_3CF_2(CF_2CF_2)_{2-8}(CH_2)_2OC(O)CH$=$CH_2$, and $F(CF(CF_3)CF_2O)_{6.85}CF(CF_3)C(O)NHCH_2CH_2OC(O)CH$=$CH_2$, wherein $R^a$ represents methyl, ethyl or n-butyl.

Second divalent units can be incorporated into fluorinated amine oxides useful for practicing the present disclosure by copolymerization of a compound of formula $CH_2=C(R')—C(O)—O-Q-Rf^1$ with a compound of formula $N(R)_2—V-Q^1C(O)—C(R^1)=CH_2$. Useful compounds of formula $N(R)_2—V-Q^1C(O)—C(R^1)=CH_2$ include aminoalkyl (meth)acrylates such as N,N-diethylaminoethylmethacrylate, N,N'-dimethylaminoethylmethacrylate and N-t-butylaminoethylmethacrylate, which are commercially available, for example, from Sigma-Aldrich and can be oxidized to amine oxides using the reagents described above, before or after copolymerizing.

Compounds comprising first and second divalent units may, in some embodiments, comprise third divalent units represented by formula:

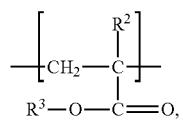

wherein each $R^2$ is independently hydrogen or methyl, and wherein each $R^3$ is independently alkyl having from 1 to 30 (in some embodiments, 1 to 25, 1 to 20, 1 to 10, 4 to 25, 8 to 25, or even 12 to 25) carbon atoms. Such third divalent units can be incorporated into a fluorinated amine oxides using a monomer selected from alkyl acrylates and methacrylates (e.g., octadecyl methacrylate, lauryl methacrylate, butyl acrylate, isobutyl methacrylate, ethylhexyl acrylate, ethylhexyl methacrylate, methyl methacrylate, hexyl acrylate, heptyl methacrylate, cyclohexyl methacrylate, or isobornyl acrylate) can be added to the reaction mixture comprising the monomers represented by formulas $CH_2=C(R^1)—C(O)—O-Q-Rf^1$ and $N(R)_2—V-Q^1C(O)—C(R^1)=CH_2$.

Fluorinated amine oxides comprising first and second divalent units useful for practicing the present disclosure may contain other units, typically in weight percents up to 20, 15, 10, or 5 percent, based on the total weight of the fluorinated amine oxide. These units may be incorporated into the compound by selecting additional components for the free-radical reaction such as allyl esters (e.g., allyl acetate and allyl heptanoate); vinyl ethers or allyl ethers (e.g., cetyl vinyl ether, dodecylvinyl ether, 2-chloroethylvinyl ether, or ethylvinyl ether); alpha-beta unsaturated nitriles (e.g., acrylonitrile, methacrylonitrile, 2-chloroacrylonitrile, 2-cyanoethyl acrylate, or alkyl cyanoacrylates); alpha-beta-unsaturated carboxylic acid derivatives (e.g., allyl alcohol, allyl glycolate, acrylamide, methacrylamide, n-diisopropyl acrylamide, or diacetoneacrylamide), styrene and its derivatives (e.g., vinyltoluene, alpha-methylstyrene, or alpha-cyanomethyl styrene); olefinic hydrocarbons which may contain at least one halogen (e.g., ethylene, propylene, isobutene, 3-chloro-1-isobutene, butadiene, isoprene, chloro and dichlorobutadiene, 2,5-dimethyl-1,5-hexadiene, and vinyl and vinylidene chloride); hydroxyalkyl-substituted polymerizable compounds (e.g., 2-hydroxyethyl methacrylate); and alkyleneoxy-containing polymerizable compounds (e.g., diethylene glycol diacrylate, tri(ethylene glycol) dimethacrylate, tri(ethylene glycol) divinyl ether, and polyoxyalkylene glycol acrylates and diacrylates (e.g., $CH_2=CHC(O)O(CH_2CH_2O)_{7-9}H$) available, for example, from Nippon Oil & Fats Company, Tokyo, Japan under the trade designation "BLEMMER"). Some useful alkyleneoxy-containing polymerizable compounds can be prepared by known methods, for example, combining one or two equivalents of acryloyl chloride or acrylic acid (or methacryloyl chloride or methacrylic acid) with a polyethylene glycol or a monoalkyl ether thereof having a molecular weight of about 200 to 10,000 grams per mole (e.g., those available from Dow Chemical Company, Midland, Mich., under the trade designation "CARBOWAX") or a block copolymer of ethylene oxide and propylene oxide having a molecular weight of about 500 to 15000 grams per mole (e.g., those available from BASF Corporation, Ludwigshafen, Germany, under the trade designation "PLURONIC"). The reaction of acrylic acid or methacyrlic acid with a poly(alkylene oxide) is typically carried out in the presence of an acid catalyst and a polymerization inhibitor at an elevated temperature in a suitable solvent; (see, e.g., Example 1 of U.S. Pat. No. 3,787,351 (Olson)).

Compounds comprising first and second divalent units useful for practicing the present disclosure can conveniently be prepared through a free radical reaction of a monomer represented by formula $CH_2=C(R^1)—C(O)—O-Q-Rf^1$ with a compound of formula $N(R)_2—V-Q^1C(O)—C(R^1)=CH_2$ and optionally a non-fluorinated monomer (e.g., an alkyl acrylate or methacrylate) using methods known in the art. Free radical initiators such as those widely known and used in the art may be used to initiate reaction of the components. Examples of free-radical initiators include azo compounds (e.g., 2,2'-azobisisobutyronitrile (AIBN), 2,2'-azobis(2-methylbutyronitrile), or azo-2-cyanovaleric acid); hydroperoxides (e.g., cumene, tert-butyl or tert-amyl hydroperoxide); dialkyl peroxides (e.g., di-tert-butyl or dicumylperoxide); peroxyesters (e.g., tert-butyl perbenzoate or di-tert-butyl peroxyphthalate); diacylperoxides (e.g., benzoyl peroxide or lauryl peroxide). Useful photoinitiators include benzoin ethers (e.g., benzoin methyl ether or benzoin butyl ether); acetophenone derivatives (e.g., 2,2-dimethoxy-2-phenylacetophenone or 2,2-diethoxyacetophenone); and acylphosphine oxide derivatives and acylphosphonate derivatives (e.g., diphenyl-2,4,6-trimethylbenzoylphosphine oxide, isopropoxyphenyl-2,4,6-trimethylbenzoylphosphine oxide, or dimethyl pivaloylphosphonate). When heated or photolyzed such free-radical initiators fragment to generate free radicals which add to ethylenically unsaturated bonds and initiate free-radical reactions.

Free-radical reactions may be carried out in any suitable solvent at any suitable concentration, (e.g., from about 5 percent to about 90 percent by weight based on the total weight of the reaction mixture). Examples of suitable solvents include aliphatic and alicyclic hydrocarbons (e.g., hexane, heptane, cyclohexane), aromatic solvents (e.g., benzene, toluene, xylene), ethers (e.g., diethyl ether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents (e.g., methylchloroform, 1,1,2-trichloro-1,2,2-trifluoroethane, trichloroethylene or trifluorotoluene), and mixtures thereof.

While it is not practical to enumerate a particular temperature suitable for all initiators and all solvents, generally suitable temperatures are in a range from about 30° C. to about 200° C. Particular temperature and solvents for use can be selected by those skilled in the art based on considerations such as the solubility of reagents, the temperature required for the use of a particular initiator, and the molecular weight desired.

Typical chain transfer agents that may be used in the preparation of polymeric fluorinated amine oxides herein include hydroxyl-substituted mercaptans (e.g., 2-mercaptoethanol, 3-mercapto-2-butanol, 3-mercapto-2-propanol, 3-mercapto-1-propanol, and 3-mercapto-1,2-propanediol (i.e., thioglycerol)); difunctional mercaptans (e.g., di(2-mercaptoethyl)sulfide); and aliphatic mercaptans (e.g., octylmercaptan, dodecylmercaptan, and octadecylmercaptan).

Adjusting, for example, the concentration and activity of the initiator, the concentration of each of the reactive monomers, the temperature, the concentration of the chain transfer agent, and the solvent using techniques known in the art can control the molecular weight of a polyacrylate copolymer.

Typically, in treatment compositions useful for practicing the methods described herein, the fluorinated amine oxide is present in the treatment composition at at least 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.5, 1, 1.5, 2, 3, 4, or 5 percent by weight, up to 5, 6, 7, 8, 9, or 10 percent by weight, based on the total weight of the treatment composition. For example, the amount of the fluorinated amine oxide in the treatment compositions may be in a range of from 0.01 to 10, 0.1 to 10, 0.1 to 5, 1 to 10, or even in a range from 1 to 5 percent by weight, based on the total weight of the treatment composition. The methods disclosed herein have been found to be surprisingly effective even with low concentrations of the fluorinated amine oxide. For example, the amount of the fluorinated amine oxide in the treatment composition may be in a range of from 0.01 to 2, 0.1 to 1.5, or 0.3 to 1, based on the total weight of the treatment composition.

Treatment compositions useful in practicing the methods disclosed herein comprise solvent. Examples of useful solvents include organic solvents, water, easily gasified fluids (e.g., supercritical or liquid carbon dioxide, ammonia, or low-molecular-weight hydrocarbons), and combinations thereof. In some embodiments, the treatment compositions comprise water and at least one organic solvent. In some embodiments, the treatment compositions are essentially free of water (i.e., contains less than 0.1 percent by weight of water, based on the total weight of the composition). In some embodiments, the solvent is a water-miscible solvent (i.e., the solvent is soluble in water in all proportions). Examples of organic solvents include polar and/or water-miscible solvents, for example, monohydroxy alcohols having from 1 to 4 or more carbon atoms (e.g., methanol, ethanol, isopropanol, propanol, or butanol); polyols such as glycols (e.g., ethylene glycol or propylene glycol), terminal alkanediols (e.g., 1,3-propanediol, 1,4-butanediol, 1,6-hexanediol, or 1,8-octanediol), polyglycols (e.g., diethylene glycol, triethylene glycol, dipropylene glycol, or poly(propylene glycol)), triols (e.g., glycerol, trimethylolpropane), or pentaerythritol; ethers such as diethyl ether, methyl t-butyl ether, tetrahydrofuran, p-dioxane, or polyol ethers (e.g., glycol ethers (e.g., ethylene glycol monobutyl ether, diethylene glycol monomethyl ether, dipropylene glycol monomethyl ether, propylene glycol monomethyl ether, 2-butoxyethanol, or those glycol ethers available under the trade designation "DOWANOL" from Dow Chemical Co., Midland, Mich.)); ketones (e.g., acetone or 2-butanone); and combinations thereof.

In some embodiments, the solvent comprises at least one of a polyol or polyol ether independently having from 2 to 25 (in some embodiments, 2 to 15, 2 to 10, 2 to 9, or even 2 to 8) carbon atoms. In some embodiments, the solvent comprises a polyol. The term "polyol" refers to an organic molecule consisting of C, H, and O atoms connected one to another by C—H, C—C, C—O, O—H single bonds, and having at least two C—O—H groups. In some embodiments, useful polyols have 2 to 25, 2 to 20, 2 to 15, 2 to 10, 2 to 8, or even 2 to 6 carbon atoms. In some embodiments, the solvent comprises a polyol ether. The term "polyol ether" refers to an organic molecule consisting of C, H, and O atoms connected one to another by C—H, C—C, C—O, O—H single bonds, and which is at least theoretically derivable by at least partial etherification of a polyol. In some embodiments, the polyol ether has at least one C—O—H group and at least one C—O—C linkage. Useful polyol ethers may have from 3 to 25 carbon atoms, 3 to 20, 3 to 15, 3 to 10, 3 to 9, 3 to 8, or even from 5 to 8 carbon atoms. In some embodiments, the polyol is at least one of ethylene glycol, propylene glycol, poly(propylene glycol), 1,3-propanediol, or 1,8-octanediol, and the polyol ether is at least one of 2-butoxyethanol, diethylene glycol monomethyl ether, ethylene glycol monobutyl ether, dipropylene glycol monomethyl ether, or 1-methoxy-2-propanol. In some embodiments, the polyol and/or polyol ether has a normal boiling point of less than 450° F. (232° C.), which may be useful, for example, to facilitate removal of the polyol and/or polyol ether from a well after treatment.

In some embodiments, useful solvents for practicing the methods disclosed herein comprise at least one of water, a monohydroxy alcohol, an ether, or a ketone, wherein the monohydroxy alcohol, the ether, and the ketone each independently have up to 4 carbon atoms. Exemplary monohydroxy alcohols having from 1 to 4 carbon atoms include methanol, ethanol, n-propanol, isopropanol, 1-butanol, 2-butanol, isobutanol, and t-butanol. Exemplary ethers having from 2 to 4 carbon atoms include diethyl ether, ethylene glycol methyl ether, tetrahydrofuran, p-dioxane, and ethylene glycol dimethyl ether. Exemplary ketones having from 3 to 4 carbon atoms include acetone, 1-methoxy-2-propanone, and 2-butanone. In some embodiments, useful solvents for practicing the methods disclosed herein comprise at least one of methanol, ethanol, isopropanol, tetrahydrofuran, or acetone.

In some embodiments of the methods disclosed herein, the treatment compositions comprise at least two organic solvents. In some embodiments, the treatment compositions comprise at least one of a polyol or polyol ether independently having from 2 to 25 (in some embodiments, 2 to 15, 2 to 10, 2 to 9, or even 2 to 8) carbon atoms and at least one of water, a monohydroxy alcohol, an ether, or a ketone, wherein the monohydroxy alcohol, the ether, and the ketone each independently have up to 4 carbon atoms. In these embodiments, in the event that a component of the solvent is a member of two functional classes, it may be used as either class but not both. For example, ethylene glycol methyl ether may be a polyol ether or a monohydroxy alcohol, but not both simultaneously. In these embodiments, each solvent component may be present as a single component or a mixture of components. In some embodiments, compositions useful for practicing the methods disclosed herein comprise at least one of a polyol or polyol ether independently having from 2 to 25 (in some embodiments, 2 to 15, 2 to 10, 2 to 9, or even 2 to 8) carbon atoms and at least one monohydroxy alcohol having up to 4 carbon atoms. In some embodiments, the solvent consists essentially of (i.e., does not contain any components that materially affect water solubilizing or displacement properties of the composition under downhole conditions) at least one of a polyol having from 2 to 25 (in some embodiments, 2 to 20, 2 to 15, 2 to 10, 2 to 9, 2 to 8, or even 2 to 6) carbon atoms or polyol ether having from 3 to 25 (in some embodiments, 3 to 20, 3 to 15, 3 to 10, 3 to 9, 3 to 8, or even from 5 to 8) carbon atoms, and at least one monohydroxy alcohol having from 1 to 4 carbon atoms, ether having from 2 to 4 carbon atoms, or ketone having from 3 to 4 carbon atoms. Typically, the solvents described herein are capable of solubilizing more brine in the presence of fluorinated amine oxide than methanol alone.

In some embodiments of methods according to the present disclosure, useful solvents at least one of at least partially solubilize or at least partially displace brine in the hydrocarbon-bearing formation. By the term "solubilizes", it is meant that the solvent dissolves the water and the salts in the brine. "At least partially solubilize" includes dissolving all or nearly all (e.g., at least 95% including up to 100%) of the water and the salts in the brine. In some embodiments, useful solvents at least partially solubilize or at least partially displace liquid hydrocarbons in the hydrocarbon-bearing formation.

For any of the embodiments wherein the treatment compositions useful for practicing the methods disclosed herein comprise at least one of a polyol or polyol ether independently having from 2 to 25 (in some embodiments, 2 to 15, 2 to 10, 2 to 9, or even 2 to 8) carbon atoms, the polyol or polyol ether is present in the treatment composition at at least 50, 55, 60, or 65 percent by weight and up to 75, 80, 85, or 90 percent by weight, based on the total weight of the composition. In some embodiments, the treatment composition comprises up to 50, 40, 30, 20, or even 10 percent by weight of a monohydroxy alcohol having up to 4 carbon atoms, based on the total weight of the treatment composition.

Useful combinations of two solvents include 1,3-propanediol (80%)/isopropanol (IPA) (20%), propylene glycol (70%)/IPA (30%), propylene glycol (90%)/IPA (10%), propylene glycol (80%)/IPA (20%), ethylene glycol (50%)/ethanol (50%), ethylene glycol (70%)/ethanol (30%), propylene glycol monobutyl ether (PGBE) (50%)/ethanol (50%), PGBE (70%)/ethanol (30%), dipropylene glycol monomethyl ether (DPGME) (50%)/ethanol (50%), DPGME (70%)/ethanol (30%), diethylene glycol monomethyl ether (DEGME) (70%)/ethanol (30%), triethylene glycol monomethyl ether (TEGME) (50%)/ethanol (50%), TEGME (70%)/ethanol (30%), 1,8-octanediol (50%)/ethanol (50%), propylene glycol (70%)/tetrahydrofuran (THF) (30%), propylene glycol (70%)/acetone (30%), propylene glycol (70%), methanol (30%), propylene glycol (60%)/IPA (40%), 2-butoxyethanol (80%)/ethanol (20%), 2-butoxyethanol (70%)/ethanol (30%), 2-butoxyethanol (60%)/ethanol (40%), propylene glycol (70%)/ethanol (30%), ethylene glycol (70%)/IPA (30%), and glycerol (70%)/IPA (30%), wherein the exemplary percentages are by weight are based on the total weight of solvent.

In some embodiments of treatment compositions disclosed herein, the solvent comprises a ketone, ether, or ester having from 4 to 10 (e.g., 5 to 10, 6 to 10, 6 to 8, or 6) carbon atoms or a hydrofluoroether or hydrofluorocarbon. In some of these embodiments, the solvent comprises two different ketones, each having 4 to 10 carbon atoms (e.g., any combination of 2-butanone, 4-methyl-2-pentanone, 3-methyl-2-pentanone, 2-methyl-3-pentanone, and 3,3-dimethyl-2-butanone). In some embodiments, the solvent further comprises at least one of water or a monohydroxy alcohol having up to 4 carbon atoms (e.g., methanol, ethanol, n-propanol, isopropanol, 1-butanol, 2-butanol, isobutanol, and t-butanol). Useful ethers having 4 to 10 carbon atoms include diethyl ether, diisopropyl ether, tetrahydrofuran, p-dioxane, and tert-butyl methyl ether. Useful esters having 4 to 10 carbon atoms include ethyl acetate, propyl acetate, and butyl acetate. Useful hydrofluoroethers may be represented by the general formula $Rf^3-[O-R_h]_a$, wherein a is an integer from 1 to 3; $Rf^3$ is a perfluoroalkyl or di- or trivalent perfluoroalkylene, each of which may be interrupted with at least one —O—; and $R_h$ is an alkyl group optionally interrupted with at least one —O—. Numerous hydrofluoroethers of this type are disclosed in U.S. Pat. No. 6,380,149 (Flynn et al.), the disclosure of which is incorporated herein by reference. In some embodiments, the hydrofluoroether is methyl perfluorobutyl ether or ethyl perfluorobutyl ether. Useful hydrofluoroethers also include hydrofluoroethers available, for example, from 3M Company, St. Paul, Minn., under the trade designations "HFE-7100" and "HFE-7200".

The ingredients for treatment compositions described herein including fluorinated amine oxides and solvents can be combined using techniques known in the art for combining these types of materials, including using conventional magnetic stir bars or mechanical mixer (e.g., in-line static mixer and recirculating pump).

The amount of solvent typically varies inversely with the amount of other components in treatment compositions useful in practicing any of the methods disclosed herein. For example, based on the total weight of the treatment composition the solvent may be present in the treatment composition in an amount of from at least 10, 20, 30, 40, or 50 percent by weight or more up to 60, 70, 80, 90, 95, 98, or even 99 percent by weight, or more.

Generally, the amounts of the fluorinated amine oxide and solvent (and type of solvent) is dependent on the particular application since conditions typically vary between wells, at different depths of individual wells, and even over time at a given location in an individual well. Advantageously, treatment methods according to the present disclosure can be customized for individual wells and conditions.

In some embodiments of the methods disclosed herein, the hydrocarbon-bearing formation includes brine. The brine present in the formation may be from a variety of sources including at least one of connate water, flowing water, mobile water, immobile water, residual water from a fracturing operation or from other downhole fluids, or crossflow water (e.g., water from adjacent perforated formations or adjacent layers in the formation). In some embodiments, the brine is connate water. In some embodiments, the brine causes water blocking (i.e., declining productivity resulting from increasing water saturation in a well). It is believed that useful treatment compositions will not undergo precipitation of the fluorinated amine oxide, dissolved salts, or other solids when the treatment compositions encounter the brine. Such precipitation may inhibit the adsorption or reaction of the fluorinated amine oxide on the formation, may clog the pores in the hydrocarbon-bearing formation thereby decreasing the permeability and the hydrocarbon and/or brine production, or a combination thereof.

In some embodiments, methods according to the present disclosure include receiving (e.g., obtaining or measuring) data comprising the temperature and the brine composition (including the brine saturation level and components of the brine) of a selected hydrocarbon-bearing formation. These data can be obtained or measured using techniques well known to one skilled in the art. In some embodiments, the methods comprise selecting a treatment composition for the hydrocarbon-bearing formation comprising the fluorinated amine oxide and solvent, based on the behavior of a mixture of the brine composition and the treatment composition. Typically, for the methods disclosed herein, a mixture of an amount of brine and the treatment composition is transparent and substantially free of precipitated solid (e.g., salts, asphaltenes, or fluorinated amine oxides). Although not wanting to be bound by theory, it is believed that the effectiveness of the methods disclosed herein for improving hydrocarbon productivity of a particular oil and/or gas well having brine accumulated in the near wellbore region will typically be determined by the ability of the treatment composition to dissolve the quantity of brine present in the near wellbore region of the well. Hence, at a given temperature greater amounts of treatment compositions having lower brine solubility (i.e., treatment compositions that can dissolve a relatively lower amount of brine) will typically be needed than in the case of treatment compositions having higher brine solubility and containing the same fluorinated amine oxide at the same concentration.

In some embodiments, a mixture of an amount of the brine composition and the treatment composition, at the temperature of the hydrocarbon-bearing formation, is transparent and free of precipitated solids. As used herein, the term transparent refers to allowing clear view of objects beyond. In some embodiments, transparent refers to liquids that are not hazy or cloudy. The term "substantially free of precipitated solid" refers to an amount of precipitated solid that does not interfere with the ability of the fluorinated amine oxide to increase the gas or liquid permeability of the hydrocarbon-bearing formation. In some embodiments, "substantially free of precipitated solid" means that no precipitated solid is visually observed. In some embodiments, "substantially free of precipitated solid" is an amount of solid that is less than 5% by weight higher than the solubility product at a given temperature and pressure.

In some embodiments, the transparent mixture of the brine composition and the treatment composition does not separate into layers, and in other embodiments, the transparent mixture of the brine composition and the treatment composition separates into at least two separate transparent liquid layers. Phase behavior of a mixture of the brine composition and the treatment composition can be evaluated prior to treating the hydrocarbon-bearing formation by obtaining a sample of the brine from the hydrocarbon-bearing formation and/or analyzing the composition of the brine from the hydrocarbon-bearing formation and preparing an equivalent brine having the same or similar composition to the composition of the brine in the formation. The brine composition and the treatment composition can be combined (e.g., in a container) at the temperature and then mixed together (e.g., by shaking or stirring). The mixture is then maintained at the temperature for a certain time period (e.g., 15 minutes), removed from the heat, and immediately visually evaluated to see if phase separation, cloudiness, or precipitation occurs. The amount of the brine composition in the mixture may be in a range from 5 to 95 percent by weight (e.g., at least 10, 20, 30, percent by weight and up to 35, 40, 45, 50, 55, 60, or 70 percent by weight) based on the total weight of the mixture.

Whether the mixture of the brine composition and the treatment composition is transparent, substantially free of precipitated solid, and separates into layers at the temperature of the hydrocarbon-bearing formation can depend on many variables (e.g., concentration of the fluorinated amine oxide, solvent composition, brine concentration and composition, hydrocarbon concentration and composition, and the presence of other components (e.g., surfactants or scale inhibitors)). Typically, for treatment compositions comprising at least one of a polyol or polyol ether described above and a monohydroxy alcohol having up to 4 carbon atoms, mixtures of the brine composition and the treatment composition do not separate into two or more layers. In some of these embodiments, the salinity of the brine is less than 150,000 ppm (e.g., less than 140,000, 130,000, 120,000, or 110,000 ppm) total dissolved salts. Typically, for treatment compositions described above comprising at least one (e.g., one or two) ketone having from 4 to 10 carbon atoms or a hydrofluoroether, mixtures of the brine composition and the treatment composition separate into two or more layers. In some of these embodiments, the salinity of the brine is greater than 100,000 ppm (e.g., greater than 110,000, 125,000, 130,000, or 150,000 ppm) total dissolved salt. Although not wishing to be bound by theory, it is believed that when two or more layers form in such mixtures, the fluorinated amine oxide preferentially partitions into a layer rich in organic solvent that has a lower concentration of dissolved salts. Typically, treatment compositions comprising at least one of a polyol or polyol ether described above and treatment compositions comprising at least one ketone having from 4 to 10 carbon atoms or a hydrofluoroether are capable of solubilizing more brine (i.e., no salt precipitation occurs) in the presence of a fluorinated amine oxide than methanol, ethanol, propanol, butanol, or acetone alone.

The phase behavior of the composition and the brine can be evaluated over an extended period of time (e.g., 1 hour, 12 hours, 24 hours, or longer) to determine if any phase separation, precipitation, or cloudiness is observed. By adjusting the relative amounts of brine (e.g., equivalent brine) and the treatment composition, it is possible to determine the maximum brine uptake capacity (above which precipitation occurs) of the treatment composition at a given temperature. Varying the temperature at which the above procedure is carried out typically results in a more complete understanding of the suitability of treatment compositions for a given well.

In addition to using a phase behavior evaluation, it is also contemplated that one may be able to obtain the compatibility information, in whole or in part, by computer simulation or by referring to previously determined, collected, and/or tabulated information (e.g., in a handbook, table, or a computer database). In some embodiments, the selecting a treatment composition comprises consulting a table of compatibility data between brines and treatment compositions at different temperatures.

In some embodiments of the methods disclosed herein, the fluorinated amine oxide is present in an amount sufficient to increase at least the gas permeability of the hydrocarbon-bearing formation. Before contacting the hydrocarbon-bearing formation with the treatment composition, the hydrocarbon-bearing formation typically has at least one of brine or liquid hydrocarbons. In some embodiments, the gas permeability after contacting the hydrocarbon-bearing formation with the treatment composition is increased by at least 5 percent (in some embodiments, by at least 10, 15, 20, 30, 40, 50, 60, 70, 80, 90, or even 100 percent or more) relative to the gas permeability of the formation before contacting the formation with the treatment composition. In some embodiments, the gas permeability is a gas relative permeability. In some embodiments, the liquid (e.g., oil or condensate) permeability in the hydrocarbon-bearing formation is also increased (in some embodiments, by at least 5, 10, 15, 20, 30, 40, 50, 60, 70, 80, 90, or even 100 percent or more) after contacting the formation with the treatment composition.

In some embodiments of the methods disclosed herein, hydrocarbon-bearing formations have both gas and liquid hydrocarbons. The liquid hydrocarbons in the hydrocarbon-bearing formation may be, for example, at least one of retrograde gas condensate or oil and may comprise, for example, at least one of methane, ethane, propane, butane, pentane, hexane, heptane, octane, nonane, decane, or higher hydrocarbons. In some of these embodiments, the liquid hydrocarbons may be condensate, black oil, or volatile oil. The term "black oil" refers to the class of crude oil typically having gas-oil ratios (GOR) less than about 2000 scf/stb (356 m$^3$/m$^3$). For example, a black oil may have a GOR in a range from about 100 (18), 200 (36), 300 (53), 400 (71), or even 500 scf/stb (89 m$^3$/m$^3$) up to about 1800 (320), 1900 (338), or even 2000 scf/stb (356 m$^3$/m$^3$). The term "volatile oil" refers to the class of crude oil typically having a GOR in a range between about 2000 and 3300 scf/stb (356 and 588 m$^3$/m$^3$). For example, a volatile oil may have a GOR in a range from about 2000 (356), 2100 (374), or even 2200 scf/stb (392 m$^3$/m$^3$) up to about 3100 (552), 3200 (570), or even 3300 scf/stb (588 m$^3$/m$^3$).

Methods according to the present disclosure may be practiced, for example, in a laboratory environment (e.g., on a core sample (i.e., a portion) of a hydrocarbon-bearing formation) or in the field (e.g., on a subterranean hydrocarbon-bearing formation situated downhole). Typically, the methods disclosed herein are applicable to downhole conditions having a pressure in a range from about 1 bar (100 kPa) to about 1000 bars (100 MPa) and have a temperature in a range from about 100° F. (37.8° C.) to 400° F. (204° C.) although the methods are not limited to hydrocarbon-bearing formations having these conditions. The skilled artisan, after reviewing the instant disclosure, will recognize that various factors may be taken into account in practice of the any of the disclosed methods including, for example, the ionic strength of the brine, pH (e.g., a range from a pH of about 4 to about 10), and the radial stress at the wellbore (e.g., about 1 bar (100 kPa) to about 1000 bars (100 MPa)).

In the field, contacting a hydrocarbon-bearing formation with a composition described herein can be carried out using methods (e.g., by pumping under pressure) well known to those skilled in the oil and gas art. Coil tubing, for example, may be used to deliver the treatment composition to a particular geological zone of a hydrocarbon-bearing formation. In some embodiments of practicing the methods described herein it may be desirable to isolate a geological zone (e.g., with conventional packers) to be contacted with the treatment composition.

Methods described herein are useful, for example on both existing and new wells. Typically, it is believed to be desirable to allow for a shut-in time after treatment compositions described herein are contacted with the hydrocarbon-bearing formations. Exemplary shut-in times include a few hours (e.g., 1 to 12 hours), about 24 hours, or even a few (e.g., 2 to 10) days. After the treatment composition has been allowed to remain in place for a selected time, the solvents present in the composition may be recovered from the formation by simply pumping fluids up tubing in a well as is commonly done to produce fluids from a formation.

In some embodiments of methods according to the present disclosure, the method comprises contacting the hydrocarbon-bearing formation with a fluid prior to contacting the hydrocarbon-bearing formation with the treatment composition, wherein the fluid at least one of partially solubilizes or partially displaces the brine in the hydrocarbon-bearing formation. In some embodiments, the fluid partially solubilizes the brine. In some embodiments, the fluid partially displaces the brine. In some embodiments, the fluid is substantially free of fluorinated surfactants. The term "substantially free of fluorinated surfactants" refers to fluid that may have a fluorinated surfactant but in an amount insufficient to alter the wettability of, for example, a hydrocarbon-bearing formation under downhole conditions. A fluid that is substantially free of fluorinated surfactants includes those that have a weight percent of such surfactants as low as 0 weight percent. The fluid may be useful for decreasing the concentration of at least one of the salts present in a brine before introducing the treatment composition to the hydrocarbon-bearing formation. The change in brine composition may change the results of a phase behavior evaluation (e.g., the combination of a treatment composition with a first brine before the fluid preflush may result in salt precipitation while the combination of the treatment composition with the brine after the fluid preflush may result in a transparent mixture with no salt precipitation.) In some embodiments, the fluid comprises at least one of toluene, diesel, heptane, octane, or condensate. In some embodiments, the fluid comprises at least one of water, methanol, ethanol, or isopropanol. In some embodiments, the fluid comprises at least one of a polyol or polyol ether independently having from 2 to 25 carbon atoms. In some embodiments, useful polyols have 2 to 20, 2 to 15, 2 to 10, 2 to 8, or even 2 to 6 carbon atoms. Exemplary useful polyols include ethylene glycol, propylene glycol, poly(propylene glycol), 1,3-propanediol, trimethylolpropane, glycerol, pentaerythritol, and 1,8-octanediol. In some embodiments, useful polyol ethers may have from 3 to 25 carbon atoms, 3 to 20, 3 to 15, 3 to 10, 3 to 8, or even from 5 to 8 carbon atoms. Exemplary useful polyol ethers include diethylene glycol monomethyl ether, ethylene glycol monobutyl ether, dipropylene glycol monomethyl ether, 2-butoxyethanol, and 1-methoxy-2-propanol. In some embodiments, the fluid comprises at least one monohydroxy alcohol, ether, or ketone independently having up to four carbon atoms. In some embodiments, the fluid comprises at least one of nitrogen, carbon dioxide, or methane.

In some embodiments, the fluid at least one of partially solubilizes or displaces the liquid hydrocarbons in the hydrocarbon-bearing formation.

In some embodiments of the methods disclosed herein, the hydrocarbon-bearing formation has at least one fracture. In some embodiments, fractured formations have at least 2, 3, 4, 5, 6, 7, 8, 9, or even 10 or more fractures. As used herein, the term "fracture" refers to a fracture that is man-made. In the field, for example, fractures are typically made by injecting a fracturing fluid into a subterranean geological formation at a rate and pressure sufficient to open a fracture therein (i.e., exceeding the rock strength). Typically, fracturing refers to hydraulic fracturing, and the fracturing fluid is a hydraulic fluid. Fracturing fluids may or may not contain proppants. Unintentional fracturing can sometimes occur, for example, during drilling of a wellbore. Unintentional fractures can be detected (e.g., by fluid loss from the wellbore) and repaired. Typically, fracturing a hydrocarbon-bearing formation refers to intentionally fracturing the formation after the wellbore is drilled. In some embodiments, hydrocarbon-bearing formations that may be treated according to the methods disclosed herein have natural fractures. Natural fractures may be formed, for example, as part of a network of fractures.

In some embodiments of the treatment methods disclosed herein, wherein contacting the formation with the treatment composition provides an increase in at least one of the gas permeability or the liquid permeability of the formation, the formation is a non-fractured formation (e.g., free of man-made fractures made by the hydraulic fracturing processes described herein). Advantageously, treatment methods disclosed herein typically provide an increase in at least one of the gas permeability or the liquid permeability of the formation without fracturing the formation.

In some of embodiments of the treatment methods disclosed herein, wherein the hydrocarbon-bearing formation has at least one fracture, the fracture has a plurality of proppants therein. Exemplary proppants known in the art include those made of sand (e.g., Ottawa, Brady or Colorado Sands, often referred to as white and brown sands having various ratios), resin-coated sand, ceramics (i.e., glasses, crystalline ceramics, glass-ceramics, and combinations thereof) such as sintered bauxite, thermoplastics, organic materials (e.g., ground or crushed nut shells, seed shells, fruit pits, and processed wood), and clay. Sand proppants are available, for example, from Badger Mining Corp., Berlin, Wis.; Borden Chemical, Columbus, Ohio; and Fairmont Minerals, Chardon, Ohio. Thermoplastic proppants are available, for example, from the Dow Chemical Company, Midland, Mich.; and BJ Services, Houston, Tex. Clay-based proppants are available, for example, from CarboCeramics, Irving, Tex; and Saint-Gobain, Courbevoie, France. Sintered bauxite ceramic proppants are available, for example, from Borovichi Refractories, Borovichi, Russia; 3M Company, St. Paul, Minn.; CarboCeramics; and Saint Gobain. Glass bubble and bead proppants are available, for example, from Diversified Industries, Sidney, British Columbia, Canada; and 3M Company.

In some embodiments, the proppants form packs within a formation and/or wellbore. Proppants may be selected to be chemically compatible with the solvents and fluorinated amine oxides described herein. The term "proppant" as used herein includes fracture proppant materials introducible into the formation as part of a hydraulic fracture treatment and sand control particulate introducible into the wellbore/formation as part of a sand control treatment such as a gravel pack or frac pack.

In some embodiments, methods according to the present disclosure include contacting the hydrocarbon-bearing formation with the treatment composition during fracturing, after fracturing, or during and after fracturing the hydrocarbon-bearing formation. In some of these embodiments, the fracturing fluid, which may contain proppants, may be aqueous (e.g., a brine) or may contain predominantly organic solvent (e.g., an alcohol or a hydrocarbon). In some embodiments, it may be desirable for the fracturing fluid to include viscosity enhancing agents (e.g., polymeric viscosifiers), electrolytes, corrosion inhibitors, scale inhibitors, and other such additives that are common to a fracturing fluid.

In some embodiments of methods of treated fractured formations, the amount of the composition introduced into the fractured formation is based at least partially on the volume of the fracture(s). The volume of a fracture can be measured using methods that are known in the art (e.g., by pressure transient testing of a fractured well). Typically, when a fracture is created in a hydrocarbon-bearing subterranean formation, the volume of the fracture can be estimated using at least one of the known volume of fracturing fluid or the known amount of proppant used during the fracturing operation. Coil tubing, for example, may be used to deliver the treatment composition to a particular fracture. In some embodiments, in practicing the methods disclosed herein it may be desirable to isolate the fracture (e.g., with conventional packers) to be contacted with the treatment composition.

In some embodiments, wherein the formation treated according to the methods described herein has at least one fracture, the fracture has a conductivity, and after the composition contacts at least one of the fracture or at least a portion of the plurality of proppants, the conductivity of the fracture is increased (e.g., by 25, 50, 75, 100, 125, 150, 175, 200, 225, 250, 275, or even by 300 percent).

The present disclosure also provides proppants treated with fluorinated amine oxides. In some embodiments such treated proppants are prepared by contacting a hydrocarbon-bearing formation with a treatment composition disclosed herein. Treated proppants may also be prepared, for example, by dissolving or dispersing the fluorinated amine oxide in a dispersing medium (e.g., water and/or organic solvent (e.g., alcohols, ketones, esters, alkanes and/or fluorinated solvents (e.g., hydrofluoroethers and/or perfluorinated carbons)) that is then applied to the particles. The amount of liquid medium used should be sufficient to allow the solution or dispersion to generally evenly wet the proppants being treated.

Typically, the concentration of the fluorinated amine oxide in the solution or dispersion is the range from about 5% to about 20% by weight, although amounts outside of this range may also be useful. The proppants are typically treated with the fluorinated amine oxide solution or dispersion at temperatures in the range from about 25° C. to about 50° C., although temperatures outside of this range may also be useful. The treatment solution or dispersion can be applied to the proppants using techniques known in the art for applying solutions or dispersions to proppants (e.g., mixing the solution or dispersion and proppants in a vessel (in some embodiments under reduced pressure) or spraying the solutions or dispersions onto the particles). After application of the treatment solution or dispersion to the particles, the liquid medium can be removed using techniques known in the art (e.g., drying the particles in an oven). Typically, about 0.1 to about 5 (in some embodiments, for example, about 0.5 to about 2) percent by weight fluorinated amine oxide is added to the particles, although amounts outside of this range may also be useful.

Referring to FIG. 1, an exemplary offshore oil platform is schematically illustrated and generally designated 10. Semi-submersible platform 12 is centered over submerged hydrocarbon-bearing formation 14 located below sea floor 16. Subsea conduit 18 extends from deck 20 of platform 12 to wellhead installation 22 including blowout preventers 24. Platform 12 is shown with hoisting apparatus 26 and derrick 28 for raising and lowering pipe strings such as work string 30.

Wellbore 32 extends through the various earth strata including hydrocarbon-bearing formation 14. Casing 34 is cemented within wellbore 32 by cement 36. Work string 30 may include various tools including, for example, sand control screen assembly 38 which is positioned within wellbore 32 adjacent to hydrocarbon-bearing formation 14. Also extending from platform 12 through wellbore 32 is fluid delivery tube 40 having fluid or gas discharge section 42 positioned adjacent to hydrocarbon-bearing formation 14, shown with production zone 48 between packers 44, 46. When it is desired to treat the near-wellbore region of hydrocarbon-bearing formation 14 adjacent to production zone 48, work string 30 and fluid delivery tube 40 are lowered through casing 34 until sand control screen assembly 38 and fluid discharge section 42 are positioned adjacent to the near-wellbore region of hydrocarbon-bearing formation 14 including perforations 50. Thereafter, a treatment composition described herein is pumped down delivery tube 40 to progressively treat the near-wellbore region of hydrocarbon-bearing formation 14.

While the drawing depicts an offshore operation, the skilled artisan will recognize that the methods for treating a production zone of a wellbore are equally well-suited for use in onshore operations. Also, while the drawing depicts a vertical well, the skilled artisan will also recognize that methods according to the present disclosure are equally well-suited for use in deviated wells, inclined wells or horizontal wells.

As shown in the Examples, below, methods according to the present disclosure are useful for changing the wettability of a variety of materials found in hydrocarbon-bearing formations, including sand and bauxite proppants. Fluorinated amine oxides have also been demonstrated to be useful for changing the wettability of carbonates as described in copending Int. Pat. Appl. Serial No. PCT/US11/66068, filed Dec. 20, 2011. Thus, the treatment methods are more versatile than other treatment methods which are effective with only certain substrates (e.g., sandstone). The durability of the treatment with amine oxides disclosed herein onto siliciclastic hydrocarbon-bearing formations is evidenced by the Examples, below, where it is shown that even after several volumes of heptane are passed through a column of sea sand, an increase in permeability after treatment is maintained. At least for those fluorinated amine oxides not having polymeric repeating units comprising amine oxide groups, the durability of the fluorinated amine oxide treatment on sea sand is unexpected, given the teaching in U.S. Pat. App. Publ. No. 2009/0281002 (Casper) that non-polymeric surfactants are disadvantageous because they tend to be washed away. Fluorinated amine oxides not having polymeric repeating units comprising amine oxide groups may be advantageous, for example, for treating low-permeability siliciclastic, hydrocarbon-bearing formations (e.g., tight gas formations), which may have permeabilities, for example, of up to 20, 15, 10, 5, 1, or 0.1 millidarcy.

Selected Embodiments of the Disclosure

In a first embodiment, the present disclosure provides a method of treating a siliciclastic, hydrocarbon-bearing formation, the method comprising contacting the siliciclastic, hydrocarbon-bearing formation with a treatment composition comprising solvent and a fluorinated amine oxide, wherein the fluorinated amine oxide does not have polymeric repeating units comprising amine oxide groups.

In a second embodiment, the present disclosure provides a method of treating a siliciclastic, hydrocarbon-bearing formation, the method comprising contacting the siliciclastic, hydrocarbon-bearing formation with a treatment composition comprising solvent and a fluorinated amine oxide, wherein the siliciclastic, hydrocarbon-bearing formation has at least one fracture, and the fracture has a plurality of proppants therein.

In a third embodiment, the present disclosure provides the method according to the first or second embodiment, wherein the solvent comprises at least one of water, a monohydroxy alcohol, an ether, a ketone, a glycol, a glycol ether, or supercritical carbon dioxide.

In a fourth embodiment, the present disclosure provides the method according to any one of the first to third embodiments, wherein the fluorinated amine oxide is represented by formula Rf-Q-N(R)$_2$—O, wherein Rf is independently fluoroalkyl having up to 10 carbon atoms or a polyfluoropolyether group;

Q is —SO$_2$—N(R')—W—, —C(O)—N(R=)—W—, alkylene, arylalkylene, or arylene, wherein alkylene and arylalkylene are each optionally interrupted by —O—, —S—, —SO$_2$—, or —C(O)— and optionally substituted by hydroxyl;

R' is hydrogen, alkyl having up to six carbon atoms, or aryl;

W is alkylene, arylalkylene, or arylene, wherein alkylene and arylalkylene are each optionally interrupted by —O— or —S— and optionally substituted by hydroxyl; and each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—.

In a fifth embodiment, the present disclosure provides the method according to the fourth embodiment, wherein Rf is perfluoroalkyl having up to 6 carbon atoms, Q is —SO$_2$—N(R')—W— or alkylene having up to four carbon atoms, wherein R' is hydrogen or alkyl having up to four carbon atoms, wherein W is alkylene having up to 4 carbon atoms, and wherein R is alkyl having up to four carbon atoms.

In a sixth embodiment, the present disclosure provides the method according to the fourth embodiment, wherein Rf is selected from the group consisting of:

$Rf^a$-(O)$_r$—CHF—(CF$_2$)$_{n'}$—;

[$Rf^b$-(O)$_r$—C(L)H—CF$_2$—O]$_m$—W"—;

CF$_3$CFH—O—(CF$_2$)$_{p'}$—;

CF$_3$—(O—CF$_2$)$_z$—; and

CF$_3$—O—(CF$_2$)$_3$—O—CF$_2$—;

wherein $Rf^a$ and $Rf^b$ independently represent a partially or fully fluorinated alkyl group having from 1 to 10 carbon atoms and optionally interrupted with at least one oxygen atom;

L is selected from the group consisting of F and CF$_3$;

W" is selected from the group consisting of alkylene and arylene;

r is 0 or 1, wherein when r is 0, then $Rf^a$ is interrupted with at least one oxygen atom;

t is 0 or 1;

m is 1, 2, or 3;

n' is 0 or 1;

each p' is independently an integer from 1 to 6; and z is an integer from 2 to 7;

wherein Q is —CO—N(R')—W—, wherein R' is hydrogen or alkyl having up to four carbon atoms, wherein W is alkylene having up to 4 carbon atoms, and wherein R is alkyl having up to four carbon atoms.

In a seventh embodiment, the present disclosure provides the method according to the fourth embodiment, wherein Rf is C$_3$F$_7$O(CF(CF$_3$)CF$_2$O)$_x$CF(CF$_3$)—, C$_3$F$_7$O (CF$_2$CF$_2$CF$_2$O)$_x$CF$_2$CF$_2$—, CF$_3$O(C$_2$F$_4$O)$_y$CF$_2$—, or CF$_3$O (CF$_2$O)$_{x'}$(C$_2$F$_4$O)$_{y'}$CF$_2$—, wherein x has an average value in a range from 3 to 50, and wherein y, x', and y' have average values in a range from 6 to 50.

In an eighth embodiment, the present disclosure provides the method according to any one of the first to third embodiments, wherein the wherein the fluorinated amine oxide is represented by formula

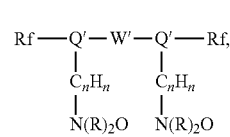

wherein

Rf is independently fluoroalkyl having up to 10 carbon atoms or a polyfluoropolyether group;

Q' is —SO$_2$N(—)(—), —(CH$_2$)$_p$CH(O—)(—), or —(CH$_2$)$_p$—CH(O—)(CH$_2$)$_p$O—, where p is an integer of 1 to 11;

W' is alkylene, arylalkylene, or arylene, wherein alkylene and arylalkylene are each optionally interrupted by —O— or —S— and optionally substituted by hydroxyl;

each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—; and each n is independently 0 to 11.

In a ninth embodiment, the present disclosure provides the method according to any of the first to eighth embodiments, wherein the fluorinated amine oxide is non-polymeric.

In a tenth embodiment, the present disclosure provides the method according to the first embodiment or any of the third to ninth embodiments except as they depend on the second embodiment, wherein the method does not include intentionally fracturing the hydrocarbon-bearing formation.

In an eleventh embodiment, the present disclosure provides the method according to the second embodiment or to the third embodiment as it depends on the second embodiment, wherein the fluorinated amine oxide is polymeric.

In a twelfth embodiment, the present disclosure provides the method according to the eleventh embodiment, wherein the fluorinated amine oxide comprises:

a first divalent unit represented by formula

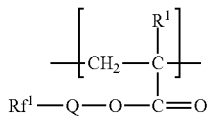

and a second divalent unit represented by formula

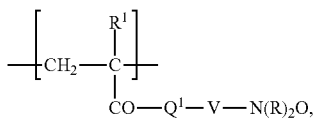

wherein each Rf$^1$ is independently fluoroalkyl having up to 10 carbon atoms or a polyfluoropolyether group;

each Q is independently —SO$_2$—N(R)—W—, —C(O)—N(R)—W—, alkylene, arylalkylene, or arylene, wherein alkylene and arylalkylene are each optionally interrupted by —O—, —S—, —SO$_2$—, or —C(O)— and optionally substituted by hydroxyl;

each W is independently alkylene, arylalkylene, or arylene, wherein alkylene and arylalkylene are each optionally interrupted by —O— or —S— and optionally substituted by hydroxyl;

each V is independently alkylene, arylalkylene, or arylene, wherein alkylene and arylalkylene are each optionally interrupted by —O— or —S— and optionally substituted by hydroxyl;

each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—;

R' is hydrogen, alkyl having up to 6 carbon atoms, or aryl;

each R' is independently hydrogen or methyl; and each Q$^1$ is independently —O—, —S—, or —N(R")—, wherein R" is hydrogen or alkyl having up to 6 carbon atoms.

In a thirteenth embodiment, the present disclosure provides the method according to the twelfth embodiment, wherein each R is independently alkyl having up to four carbon atoms.

In a fourteenth embodiment, the present disclosure provides the method according to the twelfth or thirteenth embodiment, wherein Q is —SO$_2$—N(R')—W—.

In a fifteenth embodiment, the present disclosure provides the method according to any one of the first to fourteenth embodiments, wherein the fluorinated amine oxide is present in the treatment composition in at up to 2 weight percent, based on the total weight of the treatment composition.

In a sixteenth embodiment, the present disclosure provides the method according to any one of the first to fifteenth embodiments, further comprising:

receiving data comprising a temperature and a brine composition of the siliciclastic, hydrocarbon-bearing formation; and selecting the treatment composition for contacting the siliciclastic, hydrocarbon-bearing formation, wherein, at the temperature, a mixture of an amount of the brine composition and the treatment composition is transparent and free of precipitated solid, and wherein the mixture does not separate into layers.

In a seventeenth embodiment, the present disclosure provides the method according to any one of the first to fifteenth embodiments, further comprising:

receiving data comprising a temperature and a brine composition of the siliciclastic, hydrocarbon-bearing formation; and selecting the treatment composition for contacting the siliciclastic, hydrocarbon-bearing formation, wherein, at the temperature, a mixture of the brine composition and the treatment composition separates into at least two separate transparent liquid layers, and wherein the mixture is free of precipitated solid.

In an eighteenth embodiment, the present disclosure provides the method according to any one of the first to fifteenth embodiments, further comprising:

receiving data comprising a temperature and a first brine composition of the siliciclastic, hydrocarbon-bearing formation;

contacting the siliciclastic, hydrocarbon-bearing formation with a fluid, wherein after the fluid contacts the siliciclastic, hydrocarbon-bearing formation, the siliciclastic, hydrocarbon-bearing formation has a second brine composition that is different from the first brine composition; and selecting the treatment composition for contacting the siliciclastic, hydrocarbon-bearing formation, wherein, at the temperature, a mixture of an amount of the second brine composition and the treatment composition is transparent and free of precipitated solid, and wherein the mixture does not separate into layers.

In a nineteenth embodiment, the present disclosure provides the method according to any one of the first to eighteenth embodiments, wherein the hydrocarbon-bearing formation is a gas producing formation penetrated by a wellbore, and wherein a region near the wellbore is contacted with the treatment composition.

In a twentieth embodiment, the present disclosure provides the method according to the nineteenth embodiment, further comprising obtaining gas from the wellbore after contacting the hydrocarbon-bearing formation with the treatment composition.

In a twenty-first embodiment, the present disclosure provides the method according to any one of the first to ninth and eleventh to fourteenth embodiments or any one of the fifteenth to twentieth embodiments except as dependent on the tenth embodiment, further comprising fracturing the siliciclastic, hydrocarbon-bearing formation, wherein contacting the hydrocarbon-bearing formation with the treatment composition is carried out during the fracturing, after the fracturing, or during and after the fracturing.

In a twenty-second embodiment, the present disclosure provides the method according to any one of the first to ninth and eleventh to fourteenth embodiments or any one of the fifteenth to twentieth embodiments except as dependent on the tenth embodiment, wherein the siliciclastic, hydrocarbon-bearing formation has at least one fracture, and wherein the fracture has a plurality of proppants therein.

In a twenty-third embodiment, the present disclosure provides the method according to the twenty-second embodiment, wherein the plurality of proppants comprises ceramic proppants.

In a twenty-fourth embodiment, the present disclosure provides the method according to the twenty-third embodiment, wherein the plurality of proppants comprises bauxite proppants (e.g., sintered bauxite proppants).

In a twenty-fifth embodiment, the present disclosure provides the method according to any one of the first to twenty-fourth embodiments, wherein before contacting the siliciclastic, hydrocarbon-bearing formation with the treatment composition, the siliciclastic, hydrocarbon-bearing formation has retrograde gas condensate, volatile oil, or black oil, and wherein the siliciclastic, hydrocarbon-bearing formation has an increase in at least a gas permeability after it is contacted with the treatment composition.

In a twenty-sixth embodiment, the present disclosure provides the method according to any preceding embodiment, wherein the fluorinated amine oxide is adsorbed on the siliciclastic, hydrocarbon-bearing formation.

In a twenty-seventh embodiment, the present disclosure provides the method according to any preceding embodiment, wherein the siliciclastic, hydrocarbon-bearing formation comprises sandstone.

In a twenty-eighth embodiment, the present disclosure provides the method according to the twenty-seventh embodiment, wherein the siliciclastic, hydrocarbon-bearing formation comprises at least 50 percent by weight sandstone, based on the total weight of the siliciclastic, hydrocarbon-bearing formation.

In a twenty-ninth embodiment, the present disclosure provides a siliciclastic, hydrocarbon-bearing formation treated according to the method of any one of the first to twenty-eighth embodiments.

Embodiments of the methods disclosed herein are further illustrated by the following examples, but the particular materials and amounts thereof recited in these examples, as well as other conditions and details, should not be construed to unduly limit this disclosure. Unless otherwise noted, all parts, percentages, ratios, etc. in the examples and the rest of the specification are by weight.

EXAMPLES

Materials:

Dimethylaminopropylamine (DMAPA) and dimethylaminoethyl methacrylate (DMAEMA) were obtained from Sigma-Aldrich, Milwaukee, Wis.

N,N-Dimethyldodecan-1-amine oxide was obtained under the trade designation "EMPIGEN OB" from Albright & Wilson, London, UK.

3-(Perfluorohexyl)propeneoxide was obtained from ABCR GmbH & Co., Germany.

Polymerization initiator "VAZO 67" was obtained from DuPont, Wilmington, Del.

Nonionic surfactant "PLURONIC L44" was obtained from BASF Corporation, Florham Park, N.J.

Bauxite proppant particles having an average particle size of about 0 5 mm were obtained from Carbo Chemicals, Aberdeen, UK, under the trade designation "CARBO PROP 16/30".

Sea sand having an average particle size from about 10 to about 20 mesh was obtained from Sigma-Aldrich, Bornem, Belgium.

In the following Preparation 2, $C_4F_9SO_2N(H)C_3H_6N(CH_3)_2$ was prepared as described in U.S. Pat. No. 5,468,353 (Anich), column 7, lines 15-42, incorporated herein by reference.

In the following Preparation 3, the methyl ester of perfluoro-3,7-dioxaoctanoic acid ($CF_3OCF_2CF_2OCF_2C(O)OCH_3$) was prepared according to the method described in U.S. Pat. App. Pub. No. 2007/0015864 (Hintzer et al.) in the Preparation of Compound 1, the disclosure of which preparation is incorporated herein by reference.

In the following Preparation 5, N-methylperfluorobutanesulfonylethyl acrylate (MeFBSEA) was prepared according to the method of U.S. Pat. No. 6,664,354 (Savu), Example 2, Parts A and B, incorporated herein by reference, except using 4270 kilograms (kg) of N-methylperfluorobutanesulfonamidoethanol, 1.6 kg of phenothiazine, 2.7 kg of methoxyhydroquinone, 1590 kg of heptane, 1030 kg of acrylic acid, 89 kg of methanesulfonic acid (instead of triflic acid), and 7590 kg of water in the procedure of Example 2B.

In the following Comparative Preparation 6, a nonionic fluorinated polymeric surfactant (hereinafter referred to as "Nonionic Fluorinated Polymeric Surfactant A") prepared according to the method described in U.S. Pat. No. 6,664,354, Example 2, Parts A and B, and Example 4, incorporated herein by reference, except using the modification in Example 2B described above, using 15.6 grams of 50/50 mineral spirits/TRIGONOX-21-050 organic peroxide initiator (tert-butyl peroxy-2-ethylhexanoate obtained from Akzo Nobel, Arnhem, The Netherlands) in place of 2,2'-azobisisobutyronitrile, and with 9.9 grams of 1-methyl-2-pyrrolidinone added to the charges in the procedure of Example 4.

Preparation 1:

$C_4F_9SO_2N(C_3H_6N(CH_3)_2O)CH_2CH_2(O(CH3)_2NC_3H_6)NSO_2C_4F_9$ was prepared according to the method described in U.S. Pat. 7,547,732 (Moore et al), in "Preparation of FC-3", incorporated herein by reference.

The product was further diluted to 1 wt % in a solvent mixture comprising 2-butoxyethanol/ethanol on a 70/30 weight ratio.

Preparation 2:

$C_4F_9SO_2NH(CH_2)_3N(CH_3)_2O$ was prepared by adding the following components to a three necked flask of 250 ml fitted with a stirrer, thermometer and condenser: 38.4 g (0.1 mole) of $C_4F_9SO_2NH(CH_2)_3N(CH_3)_2$, 40 g ethanol and 17 g (0.15 mole) of a 30% solution of $H_2O_2$ in water. The reaction mixture was heated up to 70° C. and reacted for 16 hours.

$C_4F_9SO_2NH(CH_2)_3N(CH_3)_2O$ was further diluted to 1 wt % in ethanol.

Preparation 3:

The following components were added to a three necked flask of 100 ml fitted with a condenser, stirrer, heating mantle and thermometer: 18.8 g (0.05 mole) of 3-(perfluorohexyl)propeneoxide and 5.1 g of DMAPA. The mixture was heated up to 70° C. under nitrogen and reacted for 4 hours. Subsequently, 23 g of ethanol and 8.5g of 30% a solution of hydrogen peroxide were added and further reacted overnight at 70° C. under air. A clear solution was obtained.

About 1 wt % of the obtained clear solution was dissolved in ethanol.

Preparation 4:

$CF_3OCF_2CF_2CF_2OCF_2C(O)NHCH_2CH_2CH_2N(CH_3)_2O$ was prepared by adding the following components to a three-necked 100-mL flask fitted with a stirrer, thermometer, and condenser: 18 grams (0.05 mole) of the methyl ester of perfluoro-3,7-dioxaoctanoic acid ($CF_3OCF_2CF_2CF_2OCF_2C(O)OCH_3$) and DMAPA (5.1 grams, 0.05 mole). The reaction mixture was heated under nitrogen at 50° C. using a heating mantle for three hours. Methanol was then removed under reduced pressure. Ethanol (24 grams) and 8.4 grams (0.075 mole) of 30% hydrogen peroxide in water were added, and the mixture was heated at 70° C. for six hours. The product, $CF_3OCF_2CF_2CF_2OCF_2C(O)NHCH_2CH_2CH_2N(CH_3)_2O$, was dissolved at 1 wt % in ethanol.

Preparation 5:

The following components were added to a three necked flask of 250 mL fitted with a condenser, stirrer, heating mantle and thermometer: 15 g of MeFBSEA, 30 g of "PLURONIC L-44", 5 g of DMAEMA, 1.5 g of 3-mercaptopropanediol, 50 g of ethanol and 0.2 g "VAZO 67". The mixture was degassed 3 times using an aspirator vacuum and nitrogen pressure and then heated up to 75° C. for 4 hours under nitrogen atmosphere. An additional 0.05 g of "VAZO 67" was added and the reaction was continued for 16 hours. The mixture was cooled to about 40° C. and 5.6 g of a 30% solution of hydrogen peroxide was added. The reaction was continued for 16 hours at 70° C. under air. A clear solution containing a polymeric fluorochemical amine-oxide was obtained.

About 1 wt % of the polymeric fluorochemical amine-oxide was dissolved in ethanol.

Comparative Preparation 6

A solvent mixture comprising 2-butoxyethanol and ethanol on a weight ratio of 70/30 was prepared. About 1 wt % (weight percent) of the "Nonionic Fluorinated Polymeric Surfactant A" was added to the solvent mixture and stirred using a magnetic stirrer and a magnetic stir bar for about 30 minutes.

Figure 2:
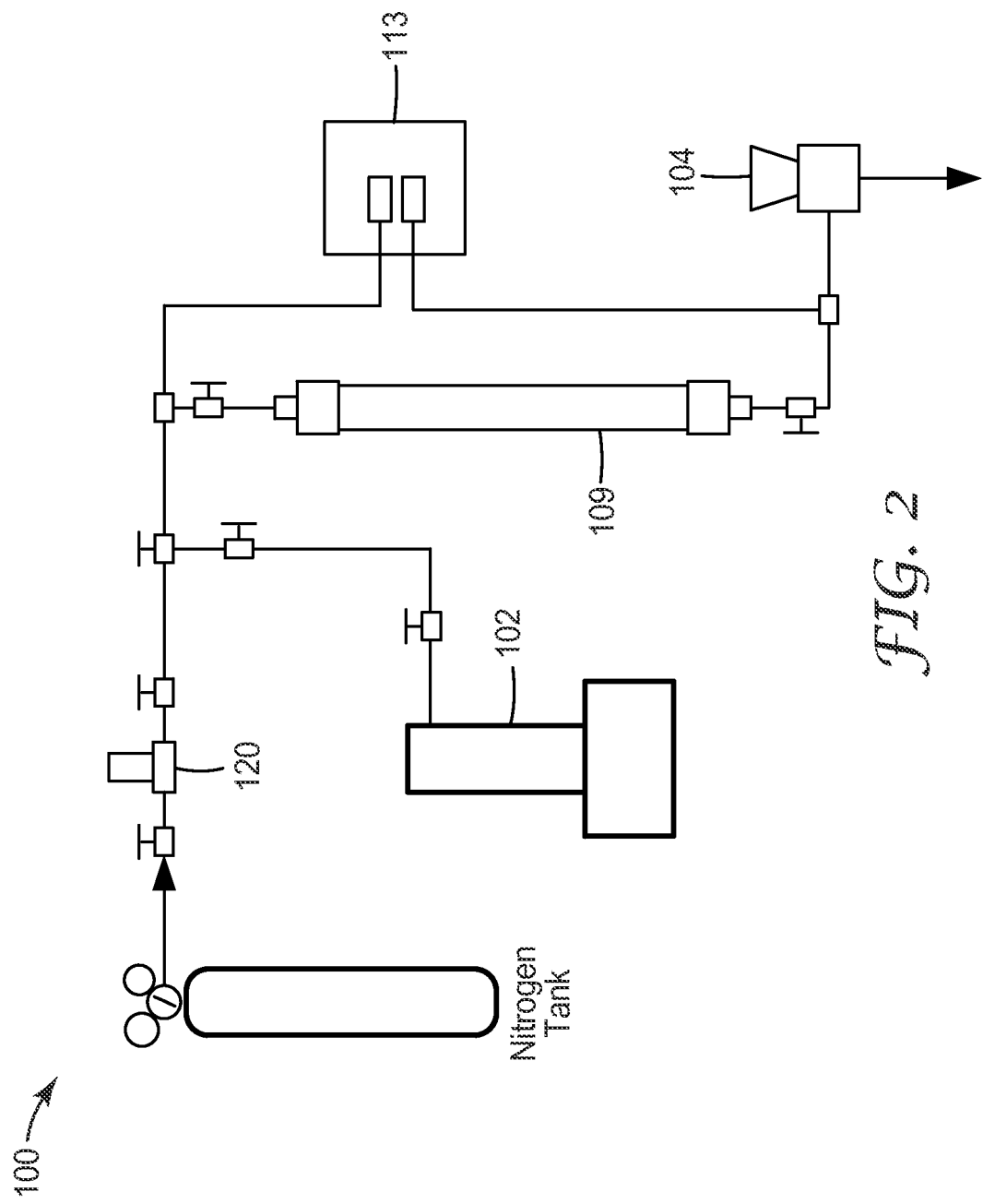
FIG. 2 is a schematic illustration of the flow apparatus used for Examples 1 to 6 and Comparative Examples A to E.

Core Flood Set Up and Procedure:

A schematic diagram of a flow apparatus 100 used to determine relative permeability of sea sand is shown in FIG. 2. Flow apparatus 100 included positive displacement pump 102 (Model Gamma/4-W 2001 PP, obtained from Prolingent AG, Regensdorf, Germany). Nitrogen gas was injected at constant rate through a gas flow controller 120 (Model DK37/MSE, Krohne, Duisburg, Germany). Pressure indicators 113, obtained from Siemens under the trade designation "SITRANS P" 0-16 bar, were used to measure the pressure drop across a substrate pack in vertical core holder 109 (20 cm by 12.5 cm$^2$) (obtained from 3M Company, Antwerp, Belgium). A back-pressure regulator (Model No. BS(H)2; obtained from RHPS, The Netherlands) 104 was used to control the flowing pressure upstream and downstream of core holder 109. Core holder 109 was heated by circulating silicone oil, heated by a heating bath obtained from Lauda, Switzerland, Model R22.

In some embodiments, the core holder was filled with sea sand and heated up to about 75° C. A pressure of about 5 bar ($5 \times 10^5$ Pa) was applied, and the back pressure was regulated in such a way that the flow of nitrogen gas through the sea sand was from about 500 to about 1000 ml/minute. The initial gas permeability was calculated using Darcy's law.

About 40-200 g of synthetic brine, prepared according to the natural composition of North Sea brine, including 5.9% sodium chloride, 1.6% calcium chloride, 0.23% magnesium chloride, and 0.05% potassium chloride and distilled water up to 100% by weight, was introduced into the core holder at about 0.5-1 ml/minute using displacement pump 102. Flow was measured and gas permeability calculated.

About 50-150 g of heptane was introduced at about 0.5 mL/minute into the core using displacement pump 102. Flow was measured and gas permeability calculated.

The fluorinated composition (treatment composition) was then injected into the core at a flow rate of 1 mL/minute. The gas permeability after treatment was calculated from the steady state pressure drop, and improvement factor was calculated as the permeability after treatment/permeability before treatment.

After the treatment, at least 10 pore volumes (400 ml) of heptane were introduced at about 0.5 mL/minute into the core using displacement pump 102.

Examples 1-3 and Comparative Examples A-C

Sea sand was treated with the following treatment compositions: ethanol (Comparative Example A), 2-butoxyethanol/ethanol (70/30 weight ratio) (Comparative Example B), "EMPIGEN OB" (Comparative Example C), and Preparations 1-3 (Examples 1-3).

Fluid phase, initial pressure (bar), pressure change (ΔP), flow rate for each injection, the amount of liquid used for each injection, the flow rate of gas through the core (Q), the gas permeability (K), and the improvement factor (PI) are shown in Table 1, below.

TABLE 1

| Examples | Fluid phase | Initial Pressure (bar) | Pressure change (ΔP) | Gas Flow (mL/min) | Amount Liquid (g) | Q (mL/sec) | K (D) | PI |
|---|---|---|---|---|---|---|---|---|
| Comp. Example A | Initial | 2.74 | 0.01 | 930 | — | 15.5 | 42.16 | — |
| | Brine | 2.82 | 0.083 | 600 | 46 | 10.42 | 3.41 | — |
| | Heptane | 2.84 | 0.089 | 510 | 80 | 8.88 | 2.71 | — |

TABLE 1-continued

| Examples | Fluid phase | Initial Pressure (bar) | Pressure change (ΔP) | Gas Flow (mL/min) | Amount Liquid (g) | Q (mL/sec) | K (D) | PI |
|---|---|---|---|---|---|---|---|---|
| | Ethanol | 2.81 | 0.037 | 520 | 160 | 8.82 | 6.48 | 2.39 |
| | Heptane | 2.89 | 0.075 | 350 | 280 | 6.05 | 2.19 | 0.81 |
| Comp. Example B | Initial | 3.84 | 0.01 | 940 | — | 15.66 | 42.6 | — |
| | Brine | 3.99 | 0.09 | 440 | 50 | 7.66 | 2.31 | — |
| | Heptane | 3.97 | 0.09 | 430 | 93 | 7.5 | 2.17 | — |
| | 2-butoxyethanol/ethanol | 3.98 | 0.047 | 440 | 125 | 7.50 | 4.34 | 2.00 |
| | Heptane | 3.99 | 0.082 | 440 | 317 | 7.63 | 2.53 | 1.16 |
| Comp. Example C | Initial | 5.1 | 0.01 | 600 | — | 10.0 | 27.2 | — |
| | Brine | 5.33 | 0.066 | 630 | 55 | 10.9 | 4.47 | — |
| | Heptane | 5.35 | 0.068 | 480 | 55 | 8.2 | 3.74 | — |
| | "EMPIGEN OB" | 5.36 | 0.027 | 360 | 97 | 6.06 | 6.1 | 1.63 |
| | Heptane | 5.37 | 0.054 | 360 | 280 | 6.18 | 3.1 | 0.83 |
| Example 1 | Initial | 5.27 | 0.01 | 900 | — | 15.0 | 40.8 | — |
| | Brine | 5.44 | 0.065 | 840 | 60 | 14.4 | 6.03 | — |
| | Heptane | 5.47 | 0.074 | 820 | 60 | 14.07 | 5.1 | — |
| | Preparation 1 | 5.48 | 0.028 | 920 | 120 | 15.6 | 15.19 | 2.97 |
| | Heptane | 5.50 | 0.035 | 900 | 270 | 15.3 | 11.89 | 2.33 |
| Example 2 | Initial | 5.1 | 0.01 | 680 | — | 11.3 | 30.8 | — |
| | Brine | 5.26 | 0.150 | 560 | 50 | 10.1 | 1.83 | — |
| | Heptane | 5.29 | 0.14 | 630 | 53 | 9.68 | 1.88 | — |
| | Preparation 2 | 5.30 | 0.092 | 750 | 100 | 13.0 | 3.84 | 2.0 |
| | Heptane | 5.29 | 0.088 | 750 | 360 | 13.0 | 4.0 | 2.21 |
| Example 3 | Initial | 5.23 | 0.01 | 580 | — | 9.7 | 26.3 | — |
| | Brine | 5.40 | 0.068 | 500 | 50 | 8.58 | 3.43 | — |
| | Heptane | 5.44 | 0.065 | 500 | 55 | 8.5 | 3.55 | — |
| | Preparation 3 | 5.46 | 0.032 | 520 | 103 | 8.83 | 7.5 | 2.10 |
| | Heptane | 5.46 | 0.033 | 540 | 265 | 9.18 | 7.56 | 2.10 |

Comparative Examples D-E and Examples 4-6

The core holder was filled with CARBO PROP and treated with the following treatment compositions: Comparative Preparation 6 (Comparative Example D), ethanol (Comparative Example D), and Preparations 2, 4, and 5 (Examples 4-6).

The core holder was filled with CARBO PROP bauxite proppant. Fluid phase, initial pressure (bar), pressure change (ΔP), flow rate for each injection, the amount of liquid used for each injection, the flow rate of gas through the core (Q), the gas permeability (K), and the improvement factor (PI) are shown in Table 2, below.

TABLE 2

| Examples | Fluid phase | Initial Pressure (bar) | Pressure change (ΔP) | Gas Flow (mL/min) | Amount Liquid (g) | Q (mL/sec) | K (D) | PI |
|---|---|---|---|---|---|---|---|---|
| Comp. Example D | Initial | 3.82 | 0.01 | 800 | — | 13.33 | 36.26 | — |
| | Brine | 3.85 | 0.085 | 630 | 43 | 10.95 | 3.50 | — |
| | Heptane | 3.87 | 0.081 | 565 | 42 | 9.79 | 3.28 | — |
| | Comp. Preparation 6 | 3.90 | 0.038 | 490 | 120 | 8.32 | 5.95 | 1.81 |
| | Heptane | 3.90 | 0.038 | 470 | 220 | 7.98 | 5.71 | 1.75 |
| Comp. Example E | Initial | 2.74 | 0.01 | 930 | — | 15.5 | 42.16 | — |
| | Brine | 2.82 | 0.083 | 600 | 46 | 10.42 | 3.41 | — |
| | Heptane | 2.84 | 0.089 | 510 | 80 | 8.88 | 2.71 | — |
| | Ethanol | 2.81 | 0.037 | 520 | 160 | 8.82 | 6.48 | 2.39 |
| | Heptane | 2.89 | 0.075 | 350 | 280 | 6.05 | 2.19 | 0.81 |
| Example 5 | Initial | 3.79 | 0.01 | 880 | — | 14.66 | 39.89 | — |
| | Brine | 3.86 | 0.07 | 700 | 66 | 12.24 | 4.75 | — |
| | Heptane | 3.86 | 0.076 | 700 | 64 | 12.1 | 4.33 | — |
| | Preparation 2 | 3.86 | 0.037 | 730 | 77 | 12.38 | 9.10 | 2.10 |
| | Heptane | 3.84 | 0.034 | 710 | 305 | 12.03 | 9.66 | 2.22 |
| Example 6 | Initial | 3.84 | 0.01 | 820 | — | 13.66 | 37.17 | — |
| | Brine | 3.95 | 0.083 | 360 | 61 | 6.25 | 2.05 | — |
| | Heptane | 3.97 | 0.080 | 270 | 82 | 4.68 | 1.59 | — |
| | Preparation 4 | 3.96 | 0.039 | 300 | 101 | 5.1 | 3.55 | 2.23 |
| | Heptane | 3.99 | 0.034 | 220 | 190 | 3.83 | 3.06 | 1.92 |
| Example 7 | Initial | 3.81 | 0.01 | 960 | — | 16.0 | 43.52 | — |
| | Brine | 3.91 | 0.070 | 540 | 57 | 9.31 | 3.61 | — |
| | Heptane | 3.88 | 0.072 | 540 | 51 | 9.32 | 3.52 | — |
| | Preparation 5 | 3.90 | 0.035 | 580 | 120 | 9.83 | 7.64 | 2.17 |
| | Heptane | 3.88 | 0.034 | 560 | 326 | 9.49 | 7.59 | 2.14 |

Figure 3:
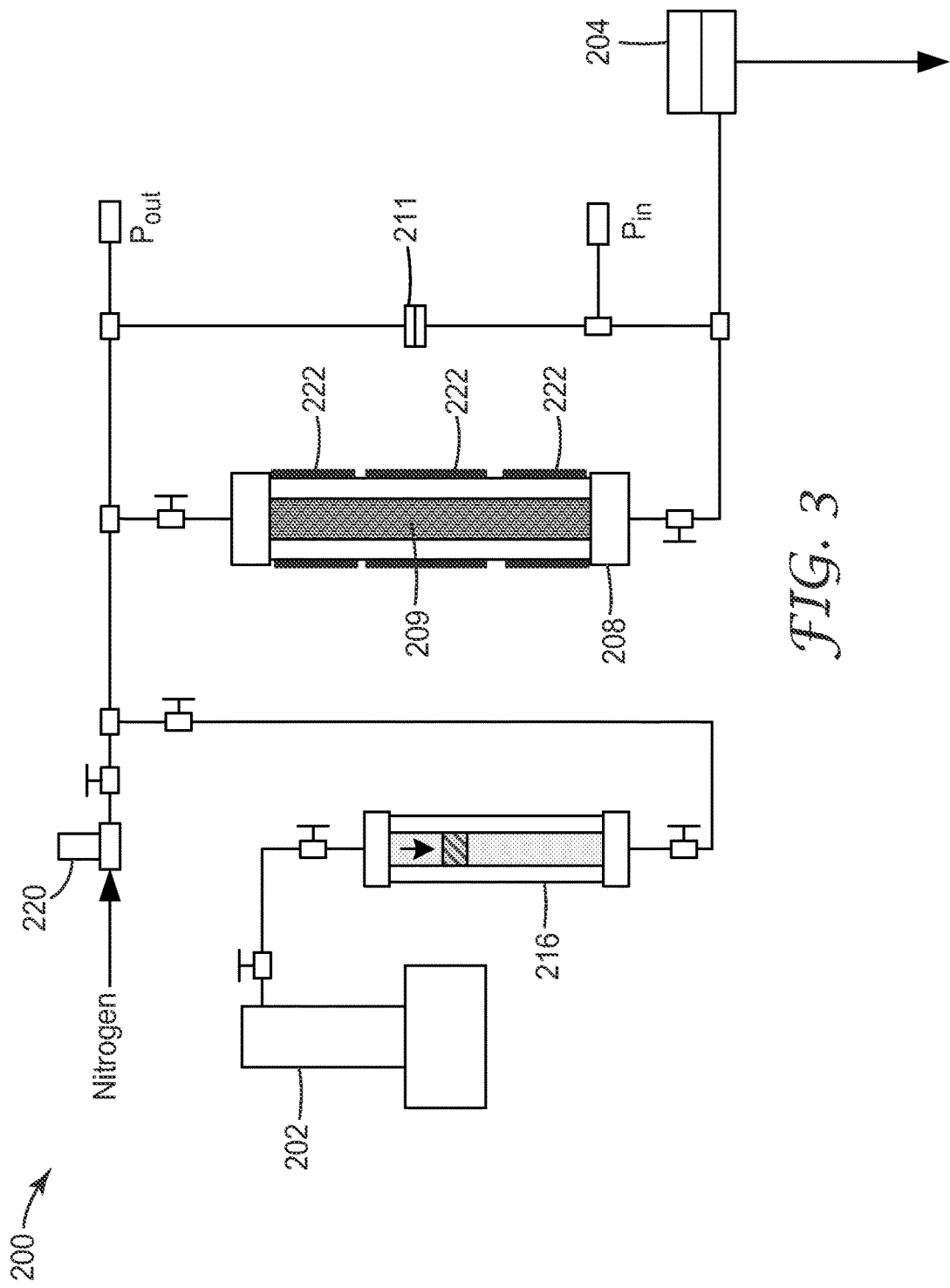
FIG. 3 is a schematic illustration of a core flood set-up that can be used to evaluate the methods disclosed herein in a laboratory.

The results of the evaluations using sea sand can be verified using core flood evaluations on sandstone core samples. A schematic diagram of a core flood apparatus 200 that can be used is shown in FIG. 3. Core flood apparatus 200 includes positive displacement pump 202 (Model QX6000SS, obtained from Chandler Engineering, Tulsa, Okla.) to inject n-heptane at constant rate into fluid accumulators 216. Nitrogen gas can be injected at constant rate through a gas flow controller 220 (Model 5850 Mass Flow Controller, Brokks Instrument, Hatfield, Pa.). A pressure port 211 on high-pressure core holder 208 (Hassler-type Model RCHR-1.0 obtained from Temco, Inc., Tulsa, Okla.) can be used to measure pressure drop across the vertical core 209. A back-pressure regulator (Model No. BP-50; obtained from Temco, Tulsa, Okla.) 204 can be used to control the flowing pressure downstream of core 209. High-pressure core holder 208 can be heated with 3 heating bands 222 (Watlow Thinband Model STB4A2AFR-2, St. Louis, Mo.).

In a typical procedure, a core can be dried for 72 hours in a standard laboratory oven at 95° C. and then wrapped in aluminum foil and heat shrink tubing. Referring again to FIG. 3, the wrapped core 209 can placed in core holder 208 at the desired temperature. An overburden pressure of, for example, 2300 psig ($1.6 \times 10^7$ Pa) can be applied. The initial single-phase gas permeability can be measured using nitrogen at low system pressures between 5 to 10 psig ($3.4 \times 10^4$ to $6.9 \times 10^4$ Pa).

Deionized water or brine can be introduced into the core 209 by the following procedure to establish the desired water saturation. The outlet end of the core holder is connected to a vacuum pump and a full vacuum can be applied for 30 minutes with the inlet closed. The inlet can be connected to a burette with the water in it. The outlet is closed and the inlet is opened to allow 2.1 mL of water to flow into the core. The inlet and the outlet valves can then be closed for the desired time. The gas permeability can be measured at the water saturation by flowing nitrogen at 500 psig ($3.4 \times 10^6$ Pa). The core holder 208 can then be heated to a higher temperature, if desired, for several hours. Nitrogen and n-heptane can be co-injected into the core at an average total flow rate in the core of, for example, 450 mL/hour at a system pressure of, for example, 900 psig ($6.2 \times 10^6$ Pa) until steady state is reached. The flow rate of nitrogen is controlled by gas flow controller 220, and the rate for n-heptane is controlled by positive displacement pump 202. The flow rates of nitrogen and n-heptane can be set such that the fractional flow of gas in the core was 0.66. The gas relative permeability before treatment can then be calculated from the steady state pressure drop. The treatment composition can then be injected into the core at a flow rate of, for example, 120 mL/hour for about 20 pore volumes. Nitrogen and n-heptane co-injection can be resumed at an average total flow rate in the core of, for example, 450 mL/hour at a system pressure of, for example, 900 psig ($6.2 \times 10^6$ Pa) until steady state is reached. The gas relative permeability after treatment can then be calculated from the steady state pressure drop.

Various modifications and alterations of this disclosure may be made by those skilled the art without departing from the scope and spirit of the disclosure, and it should be understood that this disclosure is not to be unduly limited to the illustrative embodiments set forth herein.

What is claimed is:

1. A method of treating a siliciclastic, hydrocarbon-bearing formation, the method comprising contacting the siliciclastic, hydrocarbon-bearing formation with a treatment composition comprising solvent and a fluorinated amine oxide, wherein the fluorinated amine oxide does not have polymeric repeating units comprising amine oxide groups.

2. The method of claim 1, wherein the siliciclastic, hydrocarbon-bearing formation has at least one fracture, and wherein the fracture has a plurality of proppants therein.

3. The method of claim 1, wherein the solvent comprises at least one of water, a monohydroxy alcohol, an ether, a ketone, a glycol, a glycol ether, or supercritical carbon dioxide.

4. The method of claim 1, wherein the fluorinated amine oxide is represented by formula

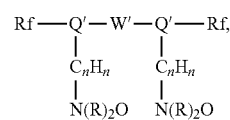

wherein
Rf is independently fluoroalkyl having up to 10 carbon atoms or a polyfluoropolyether group;
Q' is —SO$_2$N(—)(—), —(CH$_2$)$_p$CH(O—)(—), or —(CH$_2$)$_p$—CH(O—)(CH$_2$)$_p$O—, where p is an integer of 1 to 11;
W' is alkylene, arylalkylene, or arylene, wherein alkylene and arylalkylene are each optionally interrupted by —O— or —S— and optionally substituted by hydroxyl;
each R is independently hydrogen, alkyl, or aryl, wherein alkyl may optionally be interrupted by —O— or substituted with hydroxyl or aryl, or two R groups taken together with the N atom to which they are attached can form a heterocyclic ring having up to six carbon atoms and optionally containing —O— or —S—; and
each n is independently 0 to 11.

5. The method of claim 1, further comprising:
receiving data comprising a temperature and a brine composition of the siliciclastic, hydrocarbon-bearing formation; and
selecting the treatment composition for contacting the siliciclastic, hydrocarbon-bearing formation, wherein, at the temperature, a mixture of an amount of the brine composition and the treatment composition is transparent and free of precipitated solid, and wherein the mixture does not separate into layers.

6. The method of claim 1, further comprising:
receiving data comprising a temperature and a brine composition of the siliciclastic, hydrocarbon-bearing formation; and
selecting the treatment composition for contacting the siliciclastic, hydrocarbon-bearing formation, wherein, at the temperature, a mixture of the brine composition and the treatment composition separates into at least two separate transparent liquid layers, and wherein the mixture is free of precipitated solid.

7. The method of claim 1, further comprising:
receiving data comprising a temperature and a first brine composition of the siliciclastic, hydrocarbon-bearing formation;
contacting the siliciclastic, hydrocarbon-bearing formation with a fluid, wherein after the fluid contacts the siliciclastic, hydrocarbon-bearing formation, the siliciclastic, hydrocarbon-bearing formation has a second brine composition that is different from the first brine composition; and selecting the treatment composition for contacting the siliciclastic, hydrocarbon-bearing formation, wherein, at the temperature, a mixture of an amount of the second brine composition and the treatment composition is transparent and free of precipitated solid, and wherein the mixture does not separate into layers.

8. The siliciclastic, hydrocarbon-bearing formation treated according to the method of claim 1.

9. The method of claim 1, wherein the siliciclastic, hydrocarbon-bearing formation comprises sandstone.

10. The method of claim 1, wherein the siliciclastic, hydrocarbon-bearing formation has at least one fracture, wherein the at least one fracture has a plurality of proppants therein, and wherein the plurality of proppants comprises ceramic proppants.

11. The method of claim 10, wherein the plurality of proppants comprises bauxite proppants.

12. The method of claim 1, wherein the fluorinated amine oxide is represented by formula $Rf-Q-N(R)_2-O$, wherein
   Rf is independently fluoroalkyl having up to 10 carbon atoms or a polyfluoropolyether group;
   Q is $-SO_2-N(R')-W-$, $-C(O)-N(R')-W-$, alkylene, arylalkylene, or arylene, wherein alkylene and arylalkylene are each optionally interrupted by $-O-$, $-S-$, $-SO_2-$ or $-C(O)-$ and optionally substituted by hydroxyl;
   R' is hydrogen, alkyl having up to six carbon atoms, or aryl;
   W is alkylene, arylalkylene, or arylene, wherein alkylene and arylalkylene are each optionally interrupted by $-O-$ or $-S-$ and optionally substituted by hydroxyl; and
   each R is independently hydrogen, alkyl, or aryl, wherein alkyl may optionally be interrupted by $-O-$ or substituted with hydroxyl or aryl, or two R groups taken together with the N atom to which they are attached can form a heterocyclic ring having up to six carbon atoms and optionally containing $-O-$ or $-S-$.

13. The method of claim 12, wherein Rf is perfluoroalkyl having up to 6 carbon atoms, Q is $-SO_2-N(R')-W-$ or alkylene having up to four carbon atoms, wherein R' is hydrogen or alkyl having up to four carbon atoms, wherein W is alkylene having up to 4 carbon atoms, and wherein R is alkyl having up to four carbon atoms.

14. The method of claim 12, wherein Rf is selected from the group consisting of:

$Rf^a-(O)_r-CHF-(CF_2)_{n'}-$;

$[Rf^b-(O)_t-C(L)H-CF_2-O]_m-W''-$;

$CF_3CFH-O-(CF_2)_{p'}$;

$CF_3-(O-CF_2)_z-$; and $CF_3-O-(CF_2)_3-O-CF_2-$;

wherein
   $Rf^a$ and $Rf^b$ independently represent a partially or fully fluorinated alkyl group having from 1 to 10 carbon atoms and optionally interrupted with at least one oxygen atom;
   L is selected from the group consisting of F and $CF_3$;
   W'' is selected from the group consisting of alkylene and arylene;
   r is 0 or 1, wherein when r is 0, then $Rf^a$ is interrupted with at least one oxygen atom;
   t is 0 or 1;
   m is 1, 2, or 3;
   n' is 0 or 1;
   each p' is independently an integer from 1 to 6; and
   z is an integer from 2 to 7;
   wherein Q is $-CO-N(R')-W-$, wherein R' is hydrogen or alkyl having up to four carbon atoms, wherein W is alkylene having up to 4 carbon atoms, and wherein R is alkyl having up to four carbon atoms.

15. The method of claim 12, wherein Rf is $C_3F_7O(CF(CF_3)CF_2O)_xCF(CF_3)-$, $C_3F_7O(CF_2CF_2CF_2O)_xCF_2CF_2-$, $CF_3O(C_2F_4O)_yCF_2-$, or $CF_3O(CF_2O)_{x'}(C_2F_4O)_{y'}CF_2-$, wherein x has an average value in a range from 3 to 50, and wherein y, x', and y' have average values in a range from 6 to 50.

16. A method of treating a siliciclastic, hydrocarbon-bearing formation, the method comprising contacting the siliciclastic, hydrocarbon-bearing formation with a treatment composition comprising solvent and a fluorinated amine oxide, wherein the siliciclastic, hydrocarbon-bearing formation has at least one fracture, wherein the fracture has a plurality of proppants therein, and wherein the fluorinated amine oxide is polymeric and comprises:

a first divalent unit represented by formula

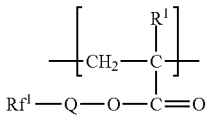

and a second divalent unit represented by formula

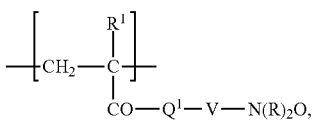

wherein
   each $Rf^1$ is independently fluoroalkyl having up to 10 carbon atoms or a polyfluoropolyether group;
   each Q is independently $-SO_2-N(R')-W-$, $-C(O)-N(R')-W-$, alkylene, arylalkylene, or arylene, wherein alkylene and arylalkylene are each optionally interrupted by $-O-$, $-S-$, $-SO_2-$ or $-C(O)-$ and optionally substituted by hydroxyl;
   each W is independently alkylene, arylalkylene, or arylene, wherein alkylene and arylalkylene are each optionally interrupted by $-O-$ or $-S-$ and optionally substituted by hydroxyl;
   each V is independently alkylene, arylalkylene, or arylene, wherein alkylene and arylalkylene are each optionally interrupted by $-O-$ or $-S-$ and optionally substituted by hydroxyl;
   each R is independently hydrogen, alkyl, or aryl, wherein alkyl may optionally be interrupted by $-O-$ or substituted with hydroxyl or aryl, or two R groups taken together with the N atom to which they are attached can form a heterocyclic ring having up to six carbon atoms and optionally containing $-O-$ or $-S-$;
   R' is hydrogen, alkyl having up to 6 carbon atoms, or aryl;
   each $R^1$ is independently hydrogen or methyl; and
   each $Q^1$ is independently $-O-$, $-S-$, or $-N(R'')-$, wherein R'' is hydrogen or alkyl having up to 6 carbon atoms.

17. The method of claim 16, wherein the plurality of proppants comprises ceramic proppants.

18. The method of claim 16, wherein the plurality of proppants comprises bauxite proppants.

19. The method of claim 16, wherein the siliciclastic, hydrocarbon-bearing formation comprises sandstone.

20. The siliciclastic, hydrocarbon-bearing formation treated according to the method of claim 16.

* * * * *